(12) United States Patent
Ghanem et al.

(10) Patent No.: US 12,721,791 B2
(45) **Date of Patent: *Sep. 1, 2026**

(54) METHOD FOR POLISHING A DENTAL CERAMIC WITH NANOPARTICLE COMPOSITION

(71) Applicant: Imam Abdulrahman Bin Faisal University, Dammam (SA)

(72) Inventors: Mohamed Amr Aly Mahrous Ghanem, Dammam (SA); Mohamed Moustafa Ahmed Gad, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 0 days.

This patent is subject to a terminal disclaimer.

(21) Appl. No.: 19/075,869

(22) Filed: Mar. 11, 2025

(65) Prior Publication Data

US 2025/0205120 A1 Jun. 26, 2025

Related U.S. Application Data

(63) Continuation of application No. 17/564,757, filed on Dec. 29, 2021, now Pat. No. 12,274,762.

(51) Int. Cl.

| | |
|---|---|
| ***A61K 6/17*** | (2020.01) |
| ***B82Y 40/00*** | (2011.01) |
| ***C09K 3/14*** | (2006.01) |

(52) U.S. Cl.

CPC .............. *A61K 6/17* (2020.01); *C09K 3/1481* (2013.01); *B82Y 40/00* (2013.01)

(58) Field of Classification Search

CPC ... A61K 6/17; A61K 6/15; A61K 6/00; A61K 8/19; A61K 2800/412; A61K 2800/40; A61K 2800/41; C09K 3/1481; C09K 3/1454; B82Y 40/00; C09G 1/02; A61Q 11/00

(Continued)

(56) References Cited

U.S. PATENT DOCUMENTS

| | | |
|---|---|---|
| 3,772,849 A | 11/1973 | Tobin, Jr. |
| 3,942,392 A | 3/1976 | Page, Jr. |

(Continued)

FOREIGN PATENT DOCUMENTS

| | | |
|---|---|---|
| CN | 112274441 A | 1/2021 |
| JP | 2007-91636 A | 4/2007 |
| RU | 2 670 443 C2 | 10/2018 |

OTHER PUBLICATIONS

Suparaksa Yamockul, et al., "Comparison of the surface roughness of feldspathic porcelain polished with a novel alumina-zirconia paste or diamond paste", Dental Materials Journal, vol. 35, Issue 3, 2016, pp. 379-385.

*Primary Examiner* — Eric J Rosen
*Assistant Examiner* — Mirayda A Aponte
(74) *Attorney, Agent, or Firm* — Oblon, McClelland, Maier & Neustadt, L.L.P.

(57) ABSTRACT

A dental polishing paste and a method of surface finishing a dental ceramic with the dental polishing paste is described. The dental polishing paste includes 60 to 90 weight percentage (wt. %) glycerin; 7.5 to 17.5 wt. % inorganic nanoparticles such as, diamond or zirconia, having a mean particle size of 5 to 25 nanometer (nm); and 2.5 to 32.5 wt. % additive, each based on a total weight of dental polishing paste.

9 Claims, 21 Drawing Sheets

(58) Field of Classification Search
USPC .................................... 433/216; 424/49, 216
See application file for complete search history.

(56) References Cited

U.S. PATENT DOCUMENTS

| | | | | |
|---|---|---|---|---|
| 9,655,817 | B2 | 5/2017 | Jahns | |
| 9,724,541 | B2 | 8/2017 | Kao | |
| 12,274,762 | B2 * | 4/2025 | Ghanem | C09K 3/1481 |
| 2002/0022563 | A1 | 2/2002 | Schweiger | |
| 2003/0224702 | A1 | 12/2003 | Roulston | |
| 2010/0196856 | A1 | 8/2010 | Mancino | |
| 2010/0254915 | A1 | 10/2010 | Kao | |
| 2013/0316305 | A1 | 11/2013 | Carden | |

* cited by examiner

METHOD FOR POLISHING A DENTAL CERAMIC WITH NANOPARTICLE COMPOSITION

CROSS-REFERENCE TO RELATED APPLICATIONS

The present application is a Continuation of U.S. application Ser. No. 17/564,757, now allowed, having a filing date of Dec. 29, 2021.

TECHNICAL FIELD

The present disclosure is directed to dental ceramics, and in particular relates to a dental polishing paste, and methods for surface finishing a dental ceramic with the dental polishing paste.

DESCRIPTION OF RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The use of dental ceramic materials in the fabrication of esthetic restorations and prostheses is in high demand in dentistry. Recently, computer-aided design/computer-aided manufacturing (CAD/CAM) technique has been widely used and has become the recommended choice to fabricate a variety of dental ceramic restorations. The popularity of CAD/CAM technology is related to several advantages such as fabrication of prosthetic restorations in short duration, improving marginal fit, adaptation of dental restorations, facilitation of dentist and lab technician communication, and reduction of chairside time for doctors as well as patients. Ceramics prepared by this technique possess superior properties such as, high tensile strength, fracture toughness, esthetic appearance, in addition to biocompatibility. Another advantage of CAD/CAM technology is that it allows fabrication of restorations in a single visit through a chairside scanning technique.

Surface polishing of ceramic restorations is carried out to remove extrinsic stains resulting from dietary intake and plaque deposition. Extrinsic stains result in bacterial accumulation and ceramic discoloration leading to loss of esthetic lifelike appearance and deterioration of biological properties of the dental ceramics. Surface adjustments of the ceramic restorations may be required clinically during an insertion visit or follow-up visits. The surface adjustments may include adjustment of an occlusion, a proximal contact, or recontouring of the ceramic restorations. Ceramics can be finished by glazing or polishing using rubber tools, discs, diamond stones, carbides, and polishing pastes to achieve a smooth shiny surface which is resistant to bacterial and plaque accumulation. Ceramic glazing is considered the most effective finishing procedure to achieve a smooth glossy surface in comparison to mechanical polishing methods. However, glazing cannot be performed intraorally since it involves firing of the ceramic restoration in a furnace. Therefore, mechanical polishing methods are widely used for performing intraoral activities. Effectiveness of surface polishing depends on several parameters such as applied pressure, speed, duration of finishing procedure, type of polishing kit and polishing paste used. Polishing pastes are highly recommended for intraoral use to regain a lustrous smooth ceramic surface.

Several studies have reported that a smoother dental ceramic surface is achieved by using different polishing systems other than self-glazing. The polishing systems include different compositions of the dental ceramics and particles size. However, precautions are taken during polishing as thinning of the ceramic restorations may occur; increasing the risk of ceramic fracture. In contrary, other studies have found no difference in surface roughness of the dental ceramics after using both; polishing pastes/kits or glazing techniques. Also, conventional dental polishing compositions are often a compromise between the cleaning efficiency, abrasiveness, and teeth sensitivity, hindering their adoption. Accordingly, there exists a need to develop dental polishing compositions that are characterized by good cleaning effect without harming the teeth.

SUMMARY

The present disclosure relates to a method of surface finishing a dental ceramic present in the oral cavity of a subject. The method comprises polishing a surface of the dental ceramic present in the oral cavity of a subject with the dental polishing paste including 60 to 90 weight percentage (wt. %) glycerin, 7.5 to 17.5 wt. % inorganic nanoparticles, that are at least one selected from the group consisting of diamond and zirconia, having a mean particle size of 5 to 25 nanometer (nm), and 2.5 to 32.5 wt. % of an additive, each based on a total weight of the dental polishing paste, to produce a polished dental ceramic, wherein the dental ceramic is selected from the group consisting of lithium disilicate and monolithic zirconia.

In some embodiments, the additive comprises at least three ingredients selected from the group consisting of a humectant, a secondary abrasive, a surfactant, a thickener, a fluoride source, a re-mineralizing agent, an anti-tartar agent, a preservative, and a flavoring agent. In some embodiments, the polishing is performed at 10,000 to 25,000 rotations per minute (rpm).

In some embodiments, the polishing is performed for 60 to 180 seconds(s).

In some embodiments, the polishing is performed using 0.5 milliliter (mL) dental polishing paste per 150 to 250 square millimeters ($mm^2$) of the surface of the dental ceramic.

In some embodiments, the dental polishing paste is used in 2 to 6 aliquots applied at regular time intervals throughout a duration of the polishing.

In some embodiments, the polishing is performed using a felt cone.

In some embodiments, the method further comprises pre-polishing the surface of the dental ceramic with a pumice slurry.

In some embodiments, the pre-polishing is performed at 10,000 to 25,000 rpm and for 30 to 90 seconds.

In some embodiments, the pre-polishing is performed using 0.5 mL pumice slurry per 150 to 250 $mm^2$ of the surface of the dental ceramic.

In some embodiments, the pre-polishing is performed using a rubber prophy cup.

In some embodiments, the polished dental ceramic has a mean surface roughness of 0.250 to 0.500 micrometer (μm).

In some embodiments, the dental ceramic is lithium disilicate, the inorganic nanoparticles are zirconia, and the polished dental ceramic has a mean surface roughness of 0.350 to 0.500 μm. In some embodiments, the dental ceramic is lithium disilicate, the inorganic nanoparticles are diamond, and the polished dental ceramic has a mean surface roughness of 0.250 to 0.425 μm.

In some embodiments, the dental ceramic is monolithic zirconia, the inorganic nanoparticles are zirconia, and the polished dental ceramic has a mean surface roughness of 0.250 to 0.425 μm.

In some embodiments, the dental ceramic is monolithic zirconia, the inorganic nanoparticles are diamond, and the polished dental ceramic has a mean surface roughness of 0.300 to 0.425 μm.

The present disclosure also relates to, a dental polishing paste. The dental polishing paste comprises 60 to 90 weight percentage (wt. %) glycerin, 7.5 to 17.5 wt. % inorganic nanoparticles, that are at least one selected from the group consisting of diamond and zirconia, having a mean particle size of 5 to 25 nm, and 2.5 to 32.5 wt. % of an additive, each based on a total weight of the dental polishing paste.

In some embodiments, the additive comprises at least three ingredients selected from the group consisting of a humectant, a secondary abrasive, a surfactant, a thickener, a fluoride source, a re-mineralizing agent, an anti-tartar agent, a preservative, and a flavoring agent.

In some embodiments, the additive comprises calcium carbonate, water, sodium lauryl sulfate, sodium monofluorophosphate, cellulose gum, tetrasodium pyrophosphate, benzyl alcohol, sodium saccharin, and xanthan gum.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
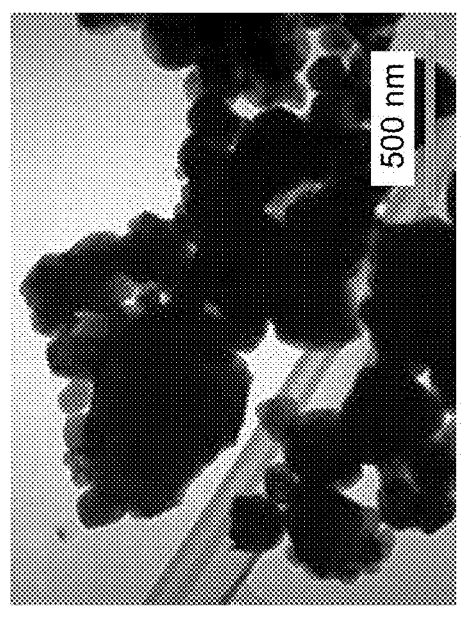
FIG. 1A-1D show Transmission Electron Microscopy (TEM) images of micro-Zirconium dioxide ($ZrO_2$), nano-$ZrO_2$, nano-silica, and nano-diamond particles, respectively, according to certain embodiments.
Figure 1B:
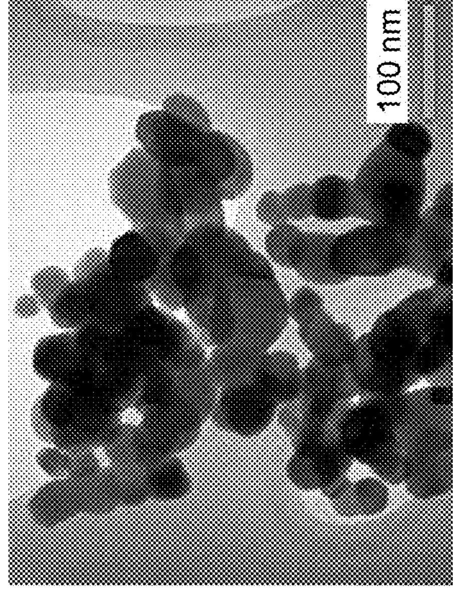
Figure 1C:
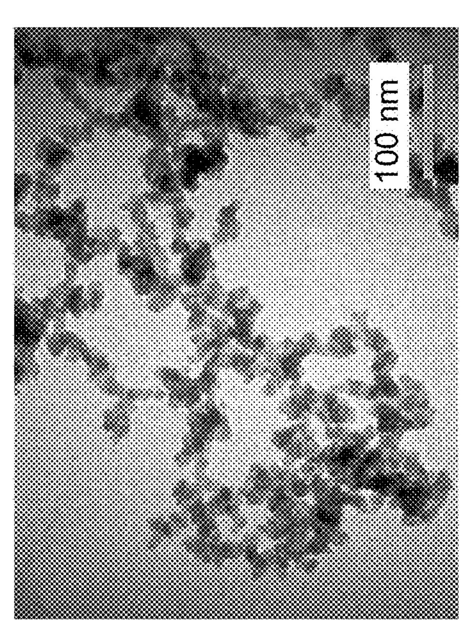
Figure 1D:
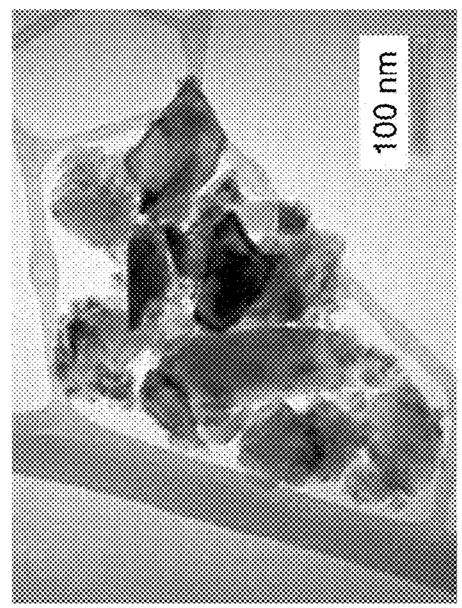

In the drawings, like reference numerals designate identical or corresponding parts throughout the several views. Further, as used herein, the words "a," "an" and the like generally carry a meaning of "one or more," unless stated otherwise.

As used herein, "polishing" refers to the implementation of making the tooth surface smooth and lustrous. Smooth may refer to the tactile sensation of a low surface roughness. Lustrous may refer to a visual indication of low surface roughness. The visual indication may be the result of interaction of light with a surface having low surface roughness. The low surface roughness may increase an amount of specular reflection and/or decrease an amount of scattering caused by the interaction. Lustrous tooth surfaces may have a shiny, pearly (or pearlescent), or vitreous (glassy) appearance. Lustrous tooth surfaces may be described as "glossy" in appearance. Smooth and/or lustrous teeth may be desirable to subjects for esthetic reasons, cultural reasons, or for health reasons.

As used herein, "dental polishing" refers to the removal of porcelain surface irregularities, plaque, calculus and stains from the exposed and unexposed surfaces of the teeth by scaling and polishing. Dental polishing is typically performed as a preventive measure for the control of local irritational factors and as an esthetic important prerequisite for any dental ceramic restoration. Dental polishing may also make the natural tooth surface smooth and lustrous as described above.

Furthermore, the terms "approximately," "approximate," "about," and similar terms generally refer to ranges that include the identified value within a margin of 20%, 10%, or preferably 5%, and any values therebetween.

Aspects of the present disclosure are directed to a dental polishing paste for polishing dental ceramics. The dental polishing paste comprises 60 to 90 weight percentage (wt. %), preferably 65 to 85 wt %, preferably 70 to 80 wt %, preferably 75 wt % glycerin and 7.5 to 17.5 wt. %, preferably 8 to 17 wt %, preferably 8.5 to 16.5 wt %, preferably 9 to 16 wt %, preferably 9.5 to 15.5 wt %, preferably 10 to 15 wt %, preferably 10.5 to 14.5 wt %, preferably 11 to 14 wt %, preferably 11.5 to 13.5 wt %, preferably 12 to 13 wt %, preferably 12.5 wt % inorganic nanoparticles, each based on a total total weight of the dental polishing paste. The inorganic nanoparticles have a mean particle size of 5 to 25 nanometer (nm), preferably 7 to 24 nm, preferably 8 to 23 nm, preferably 9 to 22 nm, preferably 10 to 21 nm, preferably 11 to 20 nm, preferably 12 to 19 nm, and are at least one selected from the group consisting of diamond and zirconia.

In general, the inorganic nanoparticles can be any shape known to one of ordinary skill in the art. Examples of suitable shapes the inorganic nanoparticles may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplatelets, nanodisks, rods (also known as nanorods), and mixtures thereof. In the case of nanorods, the rod shape may be defined by a ratio of a rod length to a rod width, the ratio being known as the aspect ratio. For inorganic nanoparticles of the current invention, nanorods should have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires and are not a shape that the inorganic nanoparticles are envisioned as having in any embodiments.

In some embodiments, the inorganic nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of inorganic nanoparticles having a different shape. As used herein, the term "non-uniform shape" refers to an average consistent shape that differs by more than 10% of the distribution of inorganic nanoparticles having a different shape. In one embodiment, the shape is uniform and at least 90% of the inorganic nanoparticles are spherical or substantially circular, and less than 10% are polygonal. In another embodiment, the shape is non-uniform and less than 90% of the inorganic nanoparticles are spherical or substantially circular, and greater than 10% are polygonal.

In embodiments where the inorganic nanoparticles are spherical, the particle size may refer to a particle diameter. In embodiments where the inorganic nanoparticles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the inorganic nanoparticles have an anisotropic shape such as nanorods, the particle size may refer to a length of the nanorod, a width of the nanorod, an average of the length and width of the nanorod. In some embodiments in which the inorganic nanoparticles have non-spherical shapes, the particle size refers to the diameter of a sphere having an equivalent volume as the particle. In some embodiments in which the inorganic nanoparticles have non-spherical shapes, the particle size refers to the diameter of a sphere having an equivalent diffusion coefficient as the particle.

In some embodiments, the inorganic nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the inorganic nanoparticles of the present disclosure are monodisperse having a particle size distribution ranging from 80% of the average particle size to 120% of the average particle size, preferably 90-110%, preferably 95-105% of the average particle size. In some embodiments, the inorganic nanoparticles are not monodisperse. In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as bulky surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In some embodiments, the particle size is determined by electron microscopy techniques such as scanning electron microscopy (SEM) or transmission electron microscopy (TEM).

The dental polishing paste further includes 2.5 to 32.5 wt. %, preferably 5 to 30 wt %, preferably 7.5 to 27.5 wt %, preferably 10 to 25 wt %, additives of the total weight of the dental polishing paste. In an embodiment, the additive comprises three or more selected from the group consisting of a humectant, a secondary abrasive, a surfactant, a thickener, a fluoride source, a re-mineralizing agent, an anti-tartar agent, a preservative, and a flavoring agent. In some embodiments, the additive comprises four or more selected from the above group. In some embodiments, the additive comprises five or more selected from the above group. In some embodiments, the additive comprises six or more selected from the above group. In some embodiments, the additive comprises seven or more selected from the above group. In some embodiments, the additive comprises a diluent. In some embodiments, the diluent is distilled water. Examples for humectants may include, but are not limited to, sorbitol, propylene glycol, and combinations thereof. Examples for surfactants may include, but are not limited to, sodium lauryl sulphate (SLS), cocamidopropyl betaine (tego betain), sodium methyl cocoyl taurate (adinol), and combinations thereof. Examples of secondary abrasives include, but are not limited to alumina, hydrated silica, dicalcium phosphate, calcium carbonate, sodium bicarbonate (baking soda), and combinations thereof. Examples of re-mineralizing agent include, but are not limited to, fluorides such as sodium monofluorophosphate, nonfluoride remineralizing agents such as alpha tricalcium phosphate (TCP), beta TCP ($\beta$-TCP), amorphous calcium phosphate, polydopamine, oligopeptides, theobromine, arginine, and self-assembling peptides. Examples of anti-tartar agents include, but are not limited to zinc citrate, sodium hexametaphosphate, tetrasodium pyrophosphate, and disodium pyrophosphate. Examples of preservatives include, but are not limited to benzoic acid, sodium benzoate, potassium sorbate, ascorbic acid, sorbic acid, domiphen and a combination thereof. Examples of flavoring agents include, but not limited to, natural flavors, natural fruit flavors, artificial flavors, artificial fruit flavors, flavor enhancers or combinations thereof. In some embodiments, the surfactant is sodium lauryl sulfate. In some embodiments, the secondary abrasive is calcium carbonate. In some embodiments, the remineralizing agent is sodium monofluorophosphate. In some embodiments, the anti-tartar agent is tetrasodium pyrophosphate. In some embodiments, the flavoring agent is sodium saccharin. In an embodiment, the additive comprises calcium carbonate, water, sodium lauryl sulfate, sodium monofluorophosphate, cellulose gum, tetrasodium pyrophosphate, benzyl alcohol, sodium saccharin, and xanthan gum.

In an exemplary embodiment, a method for surface finishing the dental ceramic present in the oral cavity of a subject is described. The dental ceramic is one of lithium disilicate and monolithic zirconia. The method includes polishing a surface of the dental ceramic with the dental polishing paste as described above. It should be understood that a "lithium disilicate dental ceramic" refers to a dental ceramic which comprises at least 51 wt %, preferably at least 55 wt %, preferably at least 60 wt %, preferably at least 65 wt %, preferably at least 70 wt %, preferably at least 75 wt %, preferably at least 80 wt %, preferably at least 85 wt %, preferably at least 90 wt %, preferably at least 95 wt %, preferably at least 99 wt % lithium disilicate. To be a lithium disilicate dental ceramic, other, non-lithium disilicate materials may be present. Similarly, a "monolithic zirconia dental ceramic" refers to a dental ceramic which comprises at least 51 wt %, preferably at least 55 wt %, preferably at least 60 wt %, preferably at least 65 wt %, preferably at least 70 wt %, preferably at least 75 wt %, preferably at least 80 wt %, preferably at least 85 wt %, preferably at least 90 wt %, preferably at least 95 wt %, preferably at least 99 wt % monolithic zirconia. To be a monolithic zirconia dental ceramic, other, non-monolithic zirconia materials may be present. In some embodiments, the dental ceramic is present in the oral cavity as a dental prosthetic which comprises the dental ceramic. In such an embodiment, the dental prosthetic may be formed from, in whole or in part, the dental ceramic. For example, the dental ceramic may form or be part of a prosthetic tooth or tooth repair.

In some embodiments, the polishing is performed at 10,000 to 25,000, preferably 11,000 to 22,000, preferably 12,000 to 20,000, preferably 13,000 to 18,000, preferably 14,000 to 16,000, preferably 15,000 revolutions per minute (rpm). In some embodiment, the polishing is performed for 60 to 180, preferably 65 to 175, preferably 70 to 170, preferably 75 to 165, preferably 80 to 160, preferably 85 to 155, preferably 90 to 150, preferably 95 to 145, preferably 100 to 140, preferably 105 to 135, preferably 110 to 130, preferably 115 to 125, preferably 120 seconds(s). In another embodiment, the polishing is performed using 0.5 milliliter (mL) dental polishing paste per 150 to 250, preferably 160 to 240, preferably 170 to 230, preferably 180 to 220, preferably 190 to 210, preferably 200 millimeter square ($mm^2$) of the surface of the dental ceramic. In an embodiment, the dental polishing paste is used in 2 to 6, preferably 3 to 5, preferably 4 aliquots applied at regular time intervals throughout a duration of the polishing. In an embodiment, the polishing is performed by a felt cone. In some embodiments, the felt cone is mounted on a low speed contra-angle handpiece with a pen grasp with an applied pressure range between 150 μm and 200 μm.

The polished dental ceramic has a mean surface roughness of 0.250 to 0.500, preferably 0.275 to 0.490, preferably 0.300 to 0.480, preferably 0.310 to 0.475, preferably 0.325 to 0.470, preferably 0.350 to 0.465, preferably 0.355 to 0.460, preferably 0.359 to 0.454 micrometer (μm). In some embodiments, the dental ceramic is lithium disilicate, the inorganic nanoparticles are zirconia, and the polished dental ceramic has a mean surface roughness of 0.350 to 0.500, preferably 0.375 to 0.495, preferably 0.400 to 0.490, preferably 0.420 to 0.485, preferably 0.425 to 0.480, preferably 0.430 to 0.475, preferably 0.435 to 0.470, preferably 0.440 to 0.465, preferably 0.445 to 0.460, preferably 0.450 to 0.455 μm. In some embodiments, the dental ceramic is lithium disilicate, the inorganic nanoparticles are diamond, and the polished dental ceramic has a mean surface roughness of 0.250 to 0.425, preferably 0.275 to 0.420, preferably 0.300 to 0.415, preferably 0.325 to 0.413, preferably 0.345 to 0.410, preferably 0.350 to 0.405, preferably 0.355 to 0.400, preferably 0.360 to 0.395, preferably 0.365 to 0.390, preferably 0.370 to 0.385, preferably 0.375 to 0.380, preferably 0.377 μm. In some embodiments, the dental ceramic is monolithic zirconia, the inorganic nanoparticles are diamond, and the polished dental ceramic has a mean surface roughness of 0.250 to 0.425, preferably 0.275 to 0.420, preferably 0.300 to 0.415, preferably 0.325 to 0.410, preferably 0.350 to 0.405, preferably 0.355 to 0.400, preferably 0.360 to 0.395, preferably 0.365 to 0.390, preferably 0.370 to 0.385, preferably 0.375 to 0.380, preferably 0.378 μm. In some embodiments, the dental ceramic is monolithic zirconia, the inorganic nanoparticles are zirconia, and the polished dental ceramic has a mean surface roughness of 0.300 to 0.425, preferably 0.325 to 0.405, preferably 0.335 to 0.395, preferably 0.340 to 0.385, preferably 0.345 to 0.375, preferably 0.350 to 0.365, preferably 0.355 to 0.360, preferably 0.359 μm.

In an embodiment, the method further comprises pre-polishing the surface of the dental ceramic with a pumice slurry prior to polishing. In an embodiment, the pre-polishing is performed at a 10,000 to 25,000, preferably 11,000 to 22,000, preferably 12,000 to 20,000, preferably 13,000 to 18,000, preferably 14,000 to 16,000, preferably 15,000 rpm and for 30 to 90, preferably 35 to 85, preferably 40 to 80, preferably 45 to 75, preferably 50 to 70, preferably 55 to 65, preferably 60 s. In an embodiment, the pre-polishing is performed using 0.5 mL pumice slurry per 150 to 250, preferably 160 to 240, preferably 170 to 230, preferably 180 to 220, preferably 190 to 210, preferably 200 $mm^2$ of the surface of the dental ceramic. In an embodiment, the pre-polishing is performed using a rubber prophy cup.

The subject may be any suitable human or animal having an oral cavity. The subject may be alive or not alive at the time of performing the method. In some embodiments, the subject is a human.

The examples below are intended to further illustrate protocols for performing the method of the present disclosure and characterizing the resulting polished dental ceramic and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

The disclosure will now be illustrated with working examples, which is intended to illustrate the working of disclosure and not intended to take restrictively to imply any limitations on the scope of the present disclosure.

Example 1

Materials and Methods

The present disclosure includes 128 specimens. The specimens were prepared from computer-aided design/computer-aided manufacturing (CAD/CAM) ceramics materials such as lithium disilicate and monolithic zirconia (n=64/per material). CAD/CAM is the use of a software to control machine tools and related ones in the manufacturing of work pieces such as dental restorations. Pre-crystalized lithium disilicate blocks having dimensions 12.4×14.5×18 millimeter (mm) (e.max CAD LT C14 A2, Ivoclar Vivadent) were sectioned into 2 mm thick specimens using a saw (IsoMet 5000 Linear Precision Saw, Buehler, IL, USA). The specimens were polished using 500 grit silicon carbide discs at 200 rpm for 1 minute under wet conditions using a polishing machine (Metaserv 250 grinder-polisher; Buehler, Lake Bluff, IL). The specimens were crystalized according to manufacturer's instructions using a ceramic furnace (Programat EP5010, Ivoclar Vivadent).

A zirconia disc in a green stage, otherwise referred to as monolithic zirconia (Cercon® HT Full Contour Zirconia, DeguDent GmbH, Hanau-Wolfgang, Germany) was sectioned using a lab saw (DW876 band saw, DEWALT, Towson, Maryland, USA) into specimens having dimensions 17.5×12.5×2.5 mm. The specimens were polished using 500 grit silicon carbide discs at 200 rpm for 30 s under wet conditions using a polishing machine. The specimens were sintered according to manufacturer's instructions using a ceramic furnace (inFire HTC speed, Sirona, DENTSPLY, NC, USA).

Specimens for each material were randomly divided into 8 groups according to surface treatment (n=8). Details about surface treatments of each group are shown in Table 1A and Table 1B.

TABLE 1A

Polishing steps according to different polishing pastes and methods with respect to groups 1-4.

| Polishing steps different polishing pastes and methods according to | Group 1 Negative control | Group 2 Glazed | Group 3 Positive control | Group 4 Diamond paste (DPs) |
|---|---|---|---|---|
| 1st | Polished using 500 grit silicon carbide discs at 200 rpm for 60 s under wet conditions using polishing machine (MetaServ 250 Grinder-Polisher with Vector Power Head, Buehler, IL, USA). Specimens were allowed to bench dry overnight before proceeding. | | | |
| 2nd | Sintering of zirconia specimens (inFire HTC speed, Sirona Dentsply, NC, USA) and crystallization of lithium disilicate specimens (Programat EP 5010, Ivoclar Vivadent) according to manufacturers' instructions. | | | |
| 3rd | No further treatment, kept as received after crystallization or sintering | Glazed using IPS Ivocolor glaze paste (Ivoclar Vivadent) according to manufacturers' instructions. | Ground using silicon carbide discs (medium grit) on the polishing machine at 200 rpm for total 60 seconds (s) and 2N of force in the form of rotational and linear motions under wet condition. | |
| 4th | | No further treatment. | Polished using rubber prophy cup and 0.1 mL of fine pumice slurry at 15,000 rpm for 60 s. Replenishing with another 0.1 mL of pumice was done for 60 s. | |
| 5th | | | Polished using rubber prophy cup and mixture of toothpaste (Colgate ™ toothpaste maximum cavity protection, Colgate ™) and glycerin (Glycerol, Merck ™, Darmstadt, Germany) at (5:2 ratio) and 15,000 rpm for 30 s. | Polished using felt cone and commercially available diamond polishing paste (Ultradent ™ diamond polish mint, 0.5 μm, Ultradent ™) |

TABLE 1B

Polishing steps according to different polishing pastes and methods with respect to groups 5-8.

| Polishing steps different polishing pastes and methods according to | Group 5 Micro-zirconia paste (ZR) | Group 6 Nano-silica paste (NS) | Group 7 Nano-diamond paste (ND) | Group 8 Nano-zirconia paste (NZR) |
|---|---|---|---|---|
| 1st | Polished using 500 grit silicon carbide discs at 200 rpm for 60 s under wet conditions using polishing machine (MetaServ 250 grinder-polisher with Vector Power Head, Buehler, IL, USA). Specimens were allowed to bench dry overnight before proceeding. | | | |
| 2nd | Sintering of zirconia specimens (inFire HTC speed, Sirona Dentsply, NC, USA) and crystallization of lithium disilicate specimens (ProgramatEP 5010, Ivoclar Vivadent) according to manufacturers' instructions. | | | |
| 3rd | Ground using silicon carbide discs (medium grit) on the polishing machine at 200 rpm for total 60 seconds and 2N of force in the form of rotational and linear motions under wet condition. | | | |

TABLE 1B-continued

Polishing steps according to different polishing pastes and methods with respect to groups 5-8.

| Polishing steps different polishing pastes and methods according to | Group 5 Micro-zirconia paste (ZR) | Group 6 Nano-silica paste (NS) | Group 7 Nano-diamond paste (ND) | Group 8 Nano-zirconia paste (NZR) |
|---|---|---|---|---|
| $4^{th}$ | Polished using rubber prophy cup and 0.1 mL of fine pumice slurry at 15,000 rpm for 60 s. Replenishing with another 0.1 mL of pumice was done for 60 s | | | |
| $5^{th}$ | Polished using felt cone and lab made paste of micro-zirconia particles (average size = 5 μm, Shanghai Richem International Co. Ltd) mixed with tooth paste and glycerin* | Polished using felt cone and lab made paste of nano-silica (average size = 12 nm, AEROSIL R812; Evonik Degussa) mixed with tooth paste and glycerin* | Polished using felt cone and lab made paste of nano-diamond (average size = 19 nm, Shanghai Richem International Co. Ltd) mixed with tooth paste and glycerin* | Polished using felt cone and lab made paste of nano-zirconia (average size = 14 nm, Shanghai Richem International Co. Ltd) mixed with tooth paste and glycerin* |

Ratio of toothpaste:glycerin:particles was 5:2:1.

Group 1 was a negative control. Group 1 was left as received after sintering or crystallization with no further surface treatment. Group 2 otherwise referred to as the glazed group. Group 2 underwent glazing after the application of a glazing paste (IPS Ivocolor, Ivoclar Vivadent) according to manufacturer's recommendations. Group 3 was a positive control. Group 3 was polished using medium grit silicon carbide discs on the polishing machine for 60 s at 200 rpm and 2 newtons (N) of force in the form of rotational and linear motions under wet conditions. Group 3 was further polished with 1:1 pumice slurry and the rubber prophy cup at 15,000 rpm for 60 s, followed by the rubber prophy cup and 0.1 mL mixture of toothpaste (Colgate™ toothpaste maximum cavity protection, Colgate™) and glycerin (glycerol, Merck™, Darmstadt, Germany) at 5:2 ratio and 15,000 rpm for 60 s.

For groups 4-8, specimens were polished using 1:1 pumice slurry and the rubber prophy cup at 15,000 rpm for 60 s followed by a diamond paste (DPs) (Ultradent diamond polish mint, 0.5 μm, Ultradent), lab made polishing pastes (microzirconia (ZR), nanosilica (NS), nanodiamond (ND) and nanozirconia (NZR)), respectively. The lab-made polishing pastes were prepared constantly. Transmission Electron Microscopy (TEM, FEI, Morgagni 268, Czech Republic at 80 kV) was performed to analyze size and shape of the four types of particles used in the lab-made polishing pastes (ZR, NZR, NS and ND) (FIG. 1). The quantity of the used powders (nano-sized and micro-sized particles, shown in Table 1B and, FIG. 1) were measured using a digital balance (DAB 220, WENSAR Mab Dab Series Analytical Balance, Mettler Tolledo, OH, USA) and mixed individually with Colgate™ toothpaste and glycerin at toothpaste:glycerin: particles ratio of 5:2:1. The used powders, Colgate™ toothpaste and glycerin together form a mixture. The mixture was stirred for 5 minutes for homogenization. A polishing procedure was initiated at 15,000 rpm after dispensing 0.1 mL of the paste and lasted for 120 s. Replenishing of the lab-made polishing pastes was done at every 30 s with 0.1 mL, and further the polishing procedure was repeated for a total of 120 s.

Rubber prophy cups/felt cones were changed for every group and for different polishing pastes. The specimens were ultrasonically cleaned in distilled water for 5 min between different polishing steps and after the polishing procedure to eliminate the polishing paste remnants. Further, the specimens were dried and underwent surface roughness reading. A single operator (Mahrous, MA) was used for performing the specimens' sectioning and polishing procedures.

Surface roughness (roughness average ($R_a$), micrometer (μm)) was corded for the specimens using a non-contact optical interferometric profilometer (Contour Gt-K 3D optical profiler; Bruker Nano Analytics). The surface roughness reading was recorded at a central area of the specimen at three locations 1 mm apart and the final surface roughness of each specimen was determined by calculating the average of three readings.

The effect of surface treatment methods on the dental ceramics; lithium disilicate and monolithic zirconia were studied using a Scanning Electron Microscope (SEM) (Inspect S50, FEI, Brno, Czech Republic). A surface morphology and a topographical assessment of lithium disilicate and monolithic zirconia; negative control and treated with different methods (the positive control, the glazed, the DPs, the NS paste, the ND paste, the ZR paste, and NZR paste) were carried out using the SEM. The specimens were mounted onto metallic SEM stubs and coated with gold (Quorum, Q150R ES, Lewes, UK). Further, observations of the specimen were obtained through the SEM. The SEM was operated at an acceleration voltage of 20 kilovolts (kv) and micrographs were taken at five different random areas of each specimen. One micrograph of each specimen was displayed at 1000× (magnification, (view area: 138 μm×138 μm)), showing the representative features of the control and treated specimens of lithium disilicate and monolithic zirconia (FIGS. 2A-2H and 3A-3H).

Data analysis was performed by using Statistical Package for the Social Sciences (SPSS-20.0) (IBM product, Chicago-USA). Numerical data based on the measurements of surface roughness ($R_a$) of the ceramics materials such as lithium disilicate and monolithic zirconia and subdivided into eight groups in relation to a polishing technique including one control group were presented as mean±standard deviation. Results were explored for normality using split-file regarding materials and Kolmogorov-Smirnov test specific to each material and within each polishing technique. Tests revealed normal distribution of the data. Two-way ANOVA was performed to compare results of $R_a$ between lithium disilicate and monolithic zirconia under the effect of polishing techniques. Post-Hoc Tukey's test was applied to compare the effect of the polishing techniques pairwise within each material. One-way Analysis of variance (ANOVA, an F-test) was applied to compare the mean difference of the polishing techniques including control group between lithium disilicate and monolithic zirconia. P-value ≤0.05 was considered statistically significant. The F-test is a statistical test in which the test statistic has an F-distribution under a null hypothesis. The null hypothesis is a type of hypothesis used in statistics which depicts no significant difference between certain characteristics of a data-generating process. In a null hypothesis significance testing, the p-value is the probability of obtaining test results at least as extreme as the results observed, under the assumption that the null hypothesis is correct.

Example 2

Surface Roughness

The effect of different polishing techniques on different materials roughness is presented in Table 2.

TABLE 2

Two-way ANOVA results for effect of different polishing techniques and different materials on roughness.

| Factors | Sum of Squares | df | Mean Squares | F | p |
|---|---|---|---|---|---|
| Material | 0.129 | 1 | 0.129 | 14.528 | 0.000* |
| Treatment | 1.103 | 7 | 0.158 | 17.705 | 0.000* |
| Material * Treatment | 0.338 | 7 | 0.048 | 5.422 | 0.000* |
| Residuals | 0.997 | 112 | 0.009 | | |

Significant p-value at α = 0.05

Referring to table 2, two-way ANOVA analysis is presented. Table 2 shows significant difference of means with regards to the ceramic material tested (F=14.53, p<0.001) as well as between the polishing techniques (F=17.7, p<0.001). The interaction effect of the ceramic material and the polishing technique was also significant (F=5.42, p<0.001). A degree of freedom (df) is the number of values which are free to vary in a data set. The mean difference of specific technique (in horizontal direction), groups with similar letters are not significantly different from each other at alpha (α)=0.05.

TABLE 3

Mean, standard deviations (SD), and statistical significance of the surface roughness of the dental ceramic with respect to the polishing techniques.

| | Polishing technique | | | | | | | |
|---|---|---|---|---|---|---|---|---|
| Materials | Negative Control Mean (SD) | Glazed Mean (SD) | positive Control Mean (SD) | DPs Mean (SD) | ZR Mean (SD) | NS Mean (SD) | ND Mean (SD) | NZR Mean (SD) |
| Lithium | 0.401 [a] | 0.406 [a] | 0.670 [b] | 0.458 [a] | 0.668 [b] | 0.393 [a] | 0.377 [a] | 0.454 [a] |
| disilicate | −0.061 | −0.073 | (0.087) | −0.056 | −0.213 | (0.088) | (0.036) | −0.071 |
| monolithic | 0.320 [a] | 0.431 [a] | 0.66 | 0.394 [a] | 0.359 [a] | 0.420 [a] | 0.378 [a] | 0.359 [a] |
| zirconia | −0.083 | −0.072 | −0.137 | −0.047 | −0.085 | −0.101 | −0.094 | −0.061 |
| P-value | 0.044* | 0.516 | 0.869 | 0.026* | 0.002* | 0.586 | 0.989 | 0.012* |

Table 3 shows significant difference of mean surface roughness ($R_a$) under specified polishing technique between lithium disilicate and monolithic zirconia materials at p≤0.05. Effect of the different polishing techniques regarding the dental ceramic revealing significant difference of mean $R_a$ of the negative control groups between lithium disilicate and monolithic zirconia (p=0.044), also significant differences between lithium disilicate and monolithic zirconia in case of DPs (p=0.026), ZR (p=0.002) and NZR (p=0.012) polishing techniques are shown. In the case of monolithic zirconia, the positive control group had the most significant effect on $R_a$ (0.660±0.137 μm) with respect to all other polishing techniques (p=0.001). Further, polishing techniques showed smoother monolithic zirconia surface with no statistical significance with respect to the other polishing techniques or to the negative control and glazed groups.

Example 3

Statistical Analysis

Post-hoc Tukey's test evaluated the effect of mean surface roughness ($R_a$) within the dental ceramic in relation to the various polishing techniques. Post-hoc Tukey's test showed the positive control and ZR polishing groups exhibiting significant surface roughness on lithium disilicate (0.670±0.087 μm, 0.668±0213 μm), respectively. The positive control and ZR polishing groups produced significantly higher surface roughness in comparison to other groups such as negative control (p=0.001), glazed (p=0.001), DPs (p=0.002, and p=0.001), NS (p=0.001), ND (p=0.001), and NZR (p=0.001) groups whereas ND polishing technique for lithium disilicate exhibited the smoothest surface among all polishing techniques with the lowest recorded $R_a$ value (0.377±0.036 μm).

Figure 2A:
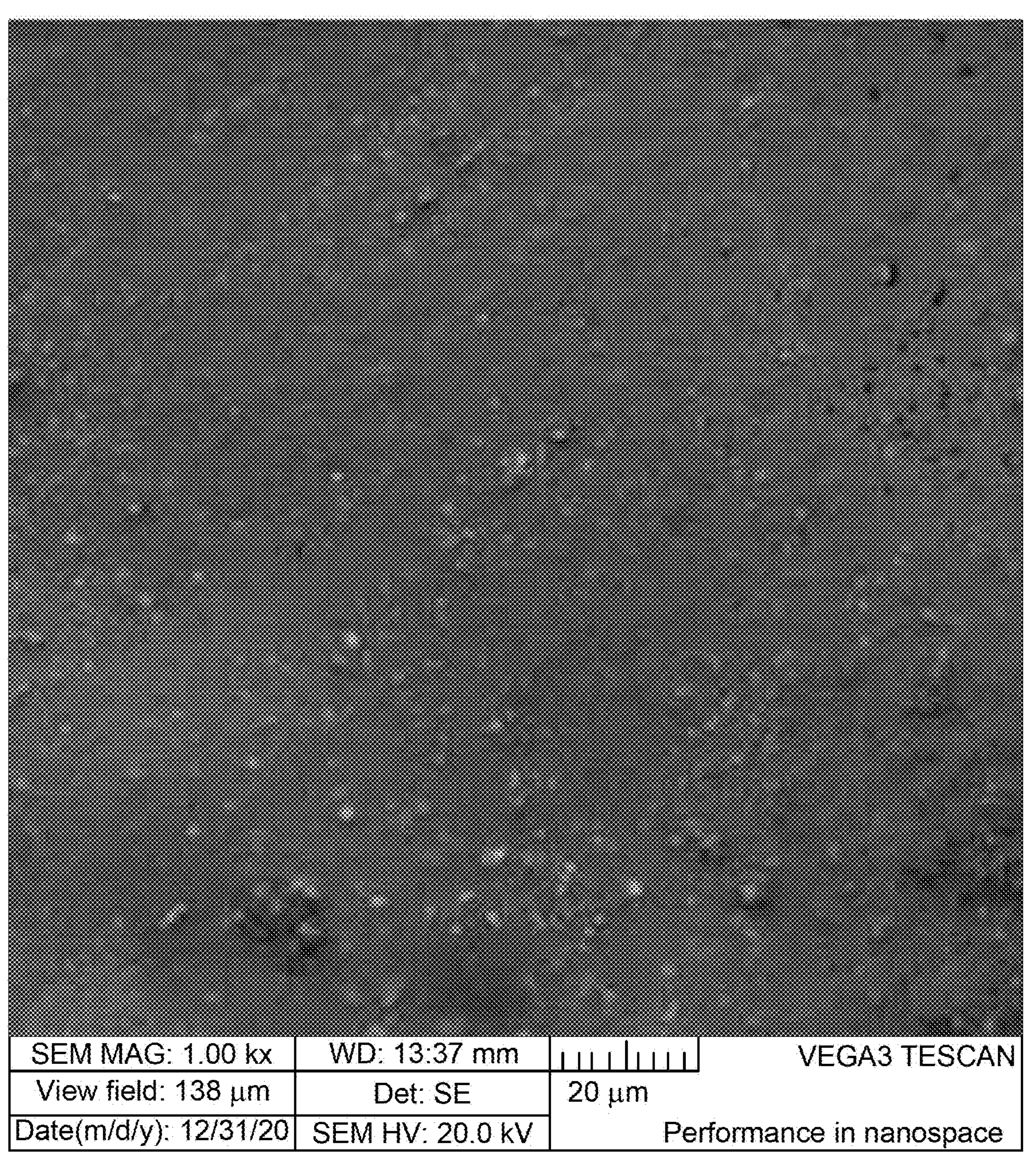
FIGS. 2A-2H are representative Scanning Electron Microscopic (SEM) images of surfaces of lithium disilicate specimens, according to certain embodiments.
Figure 2B:
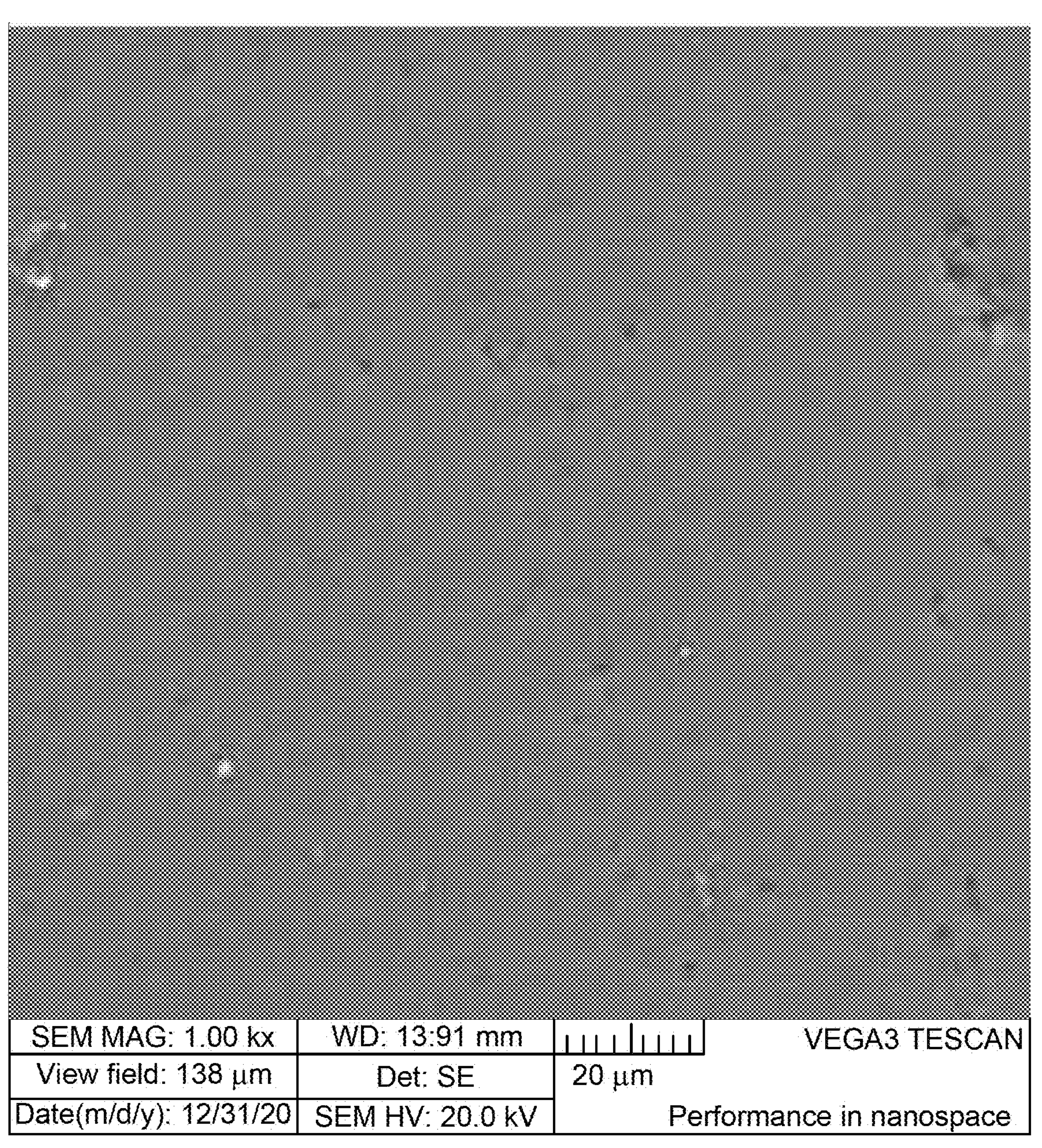
Figure 2C:
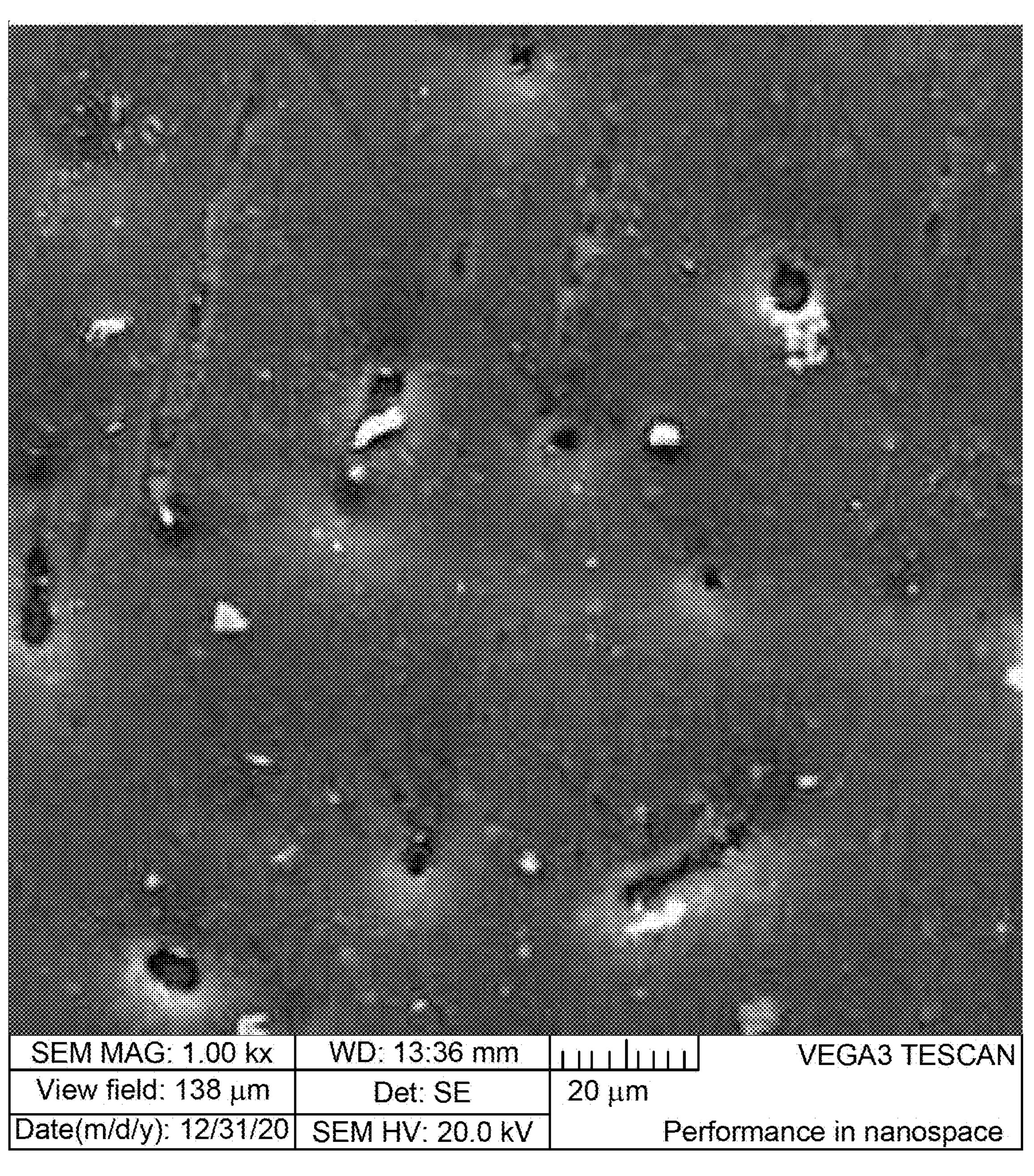
Figure 2D:
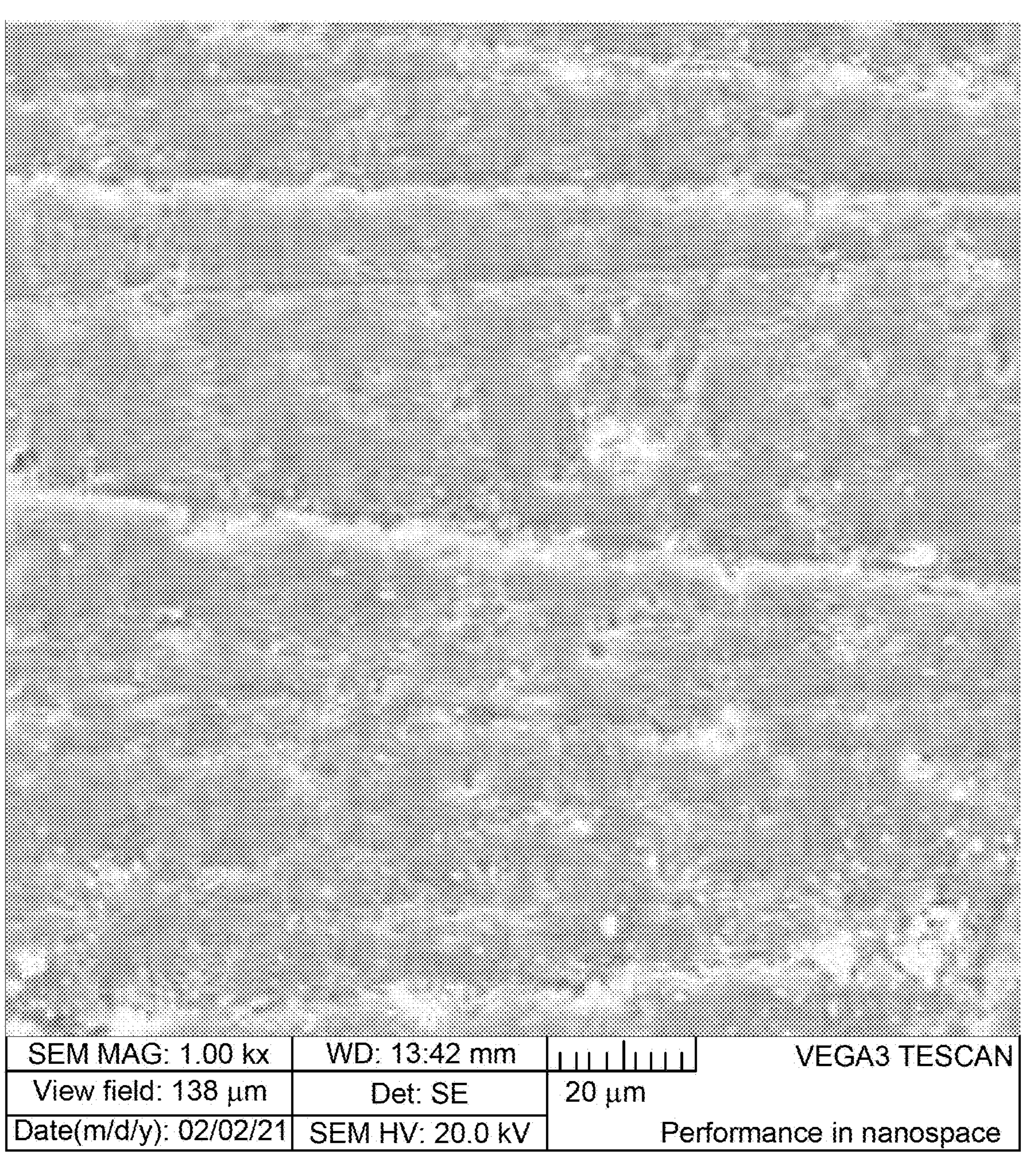
Figure 2E:
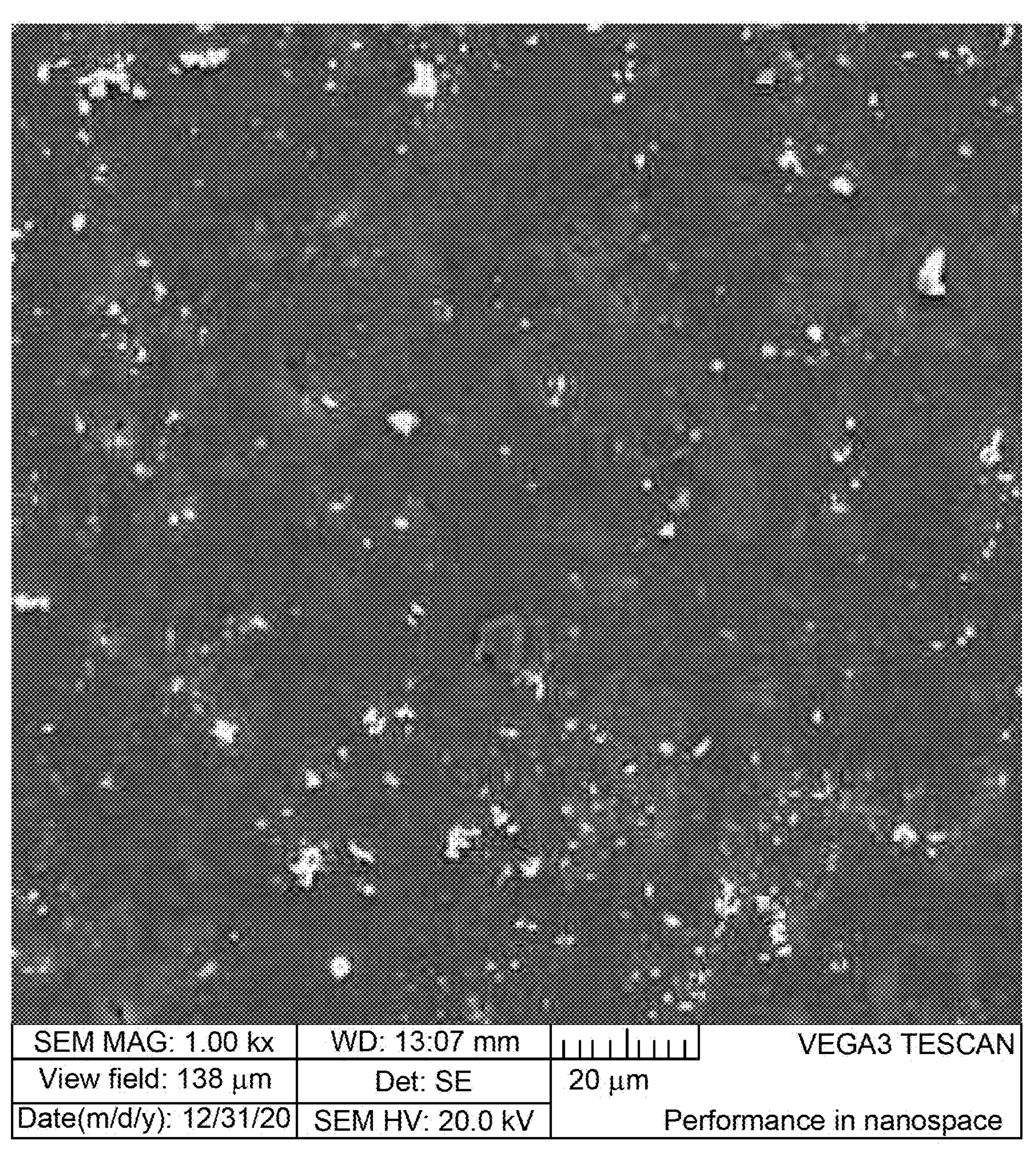
Figure 2F:
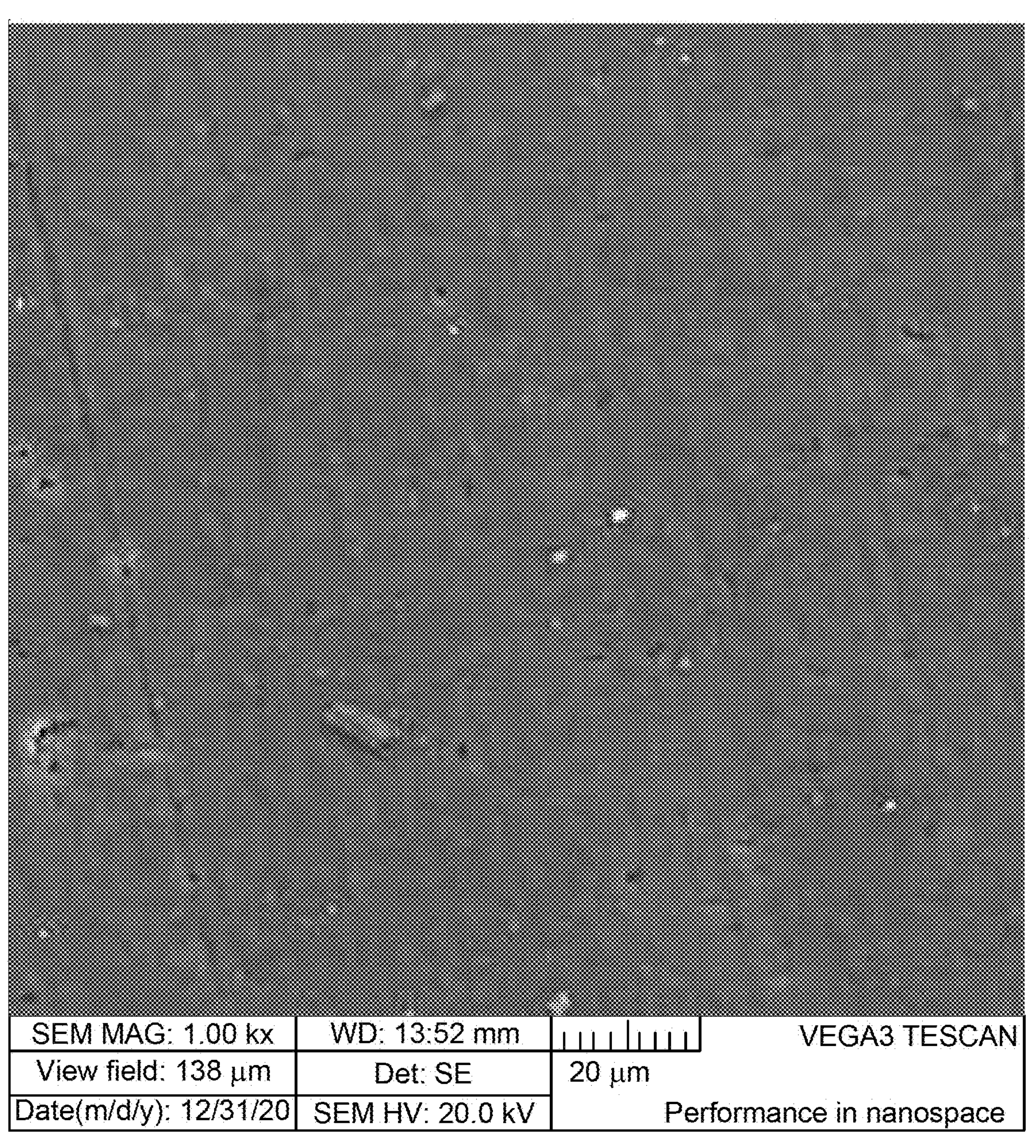
Figure 2G:
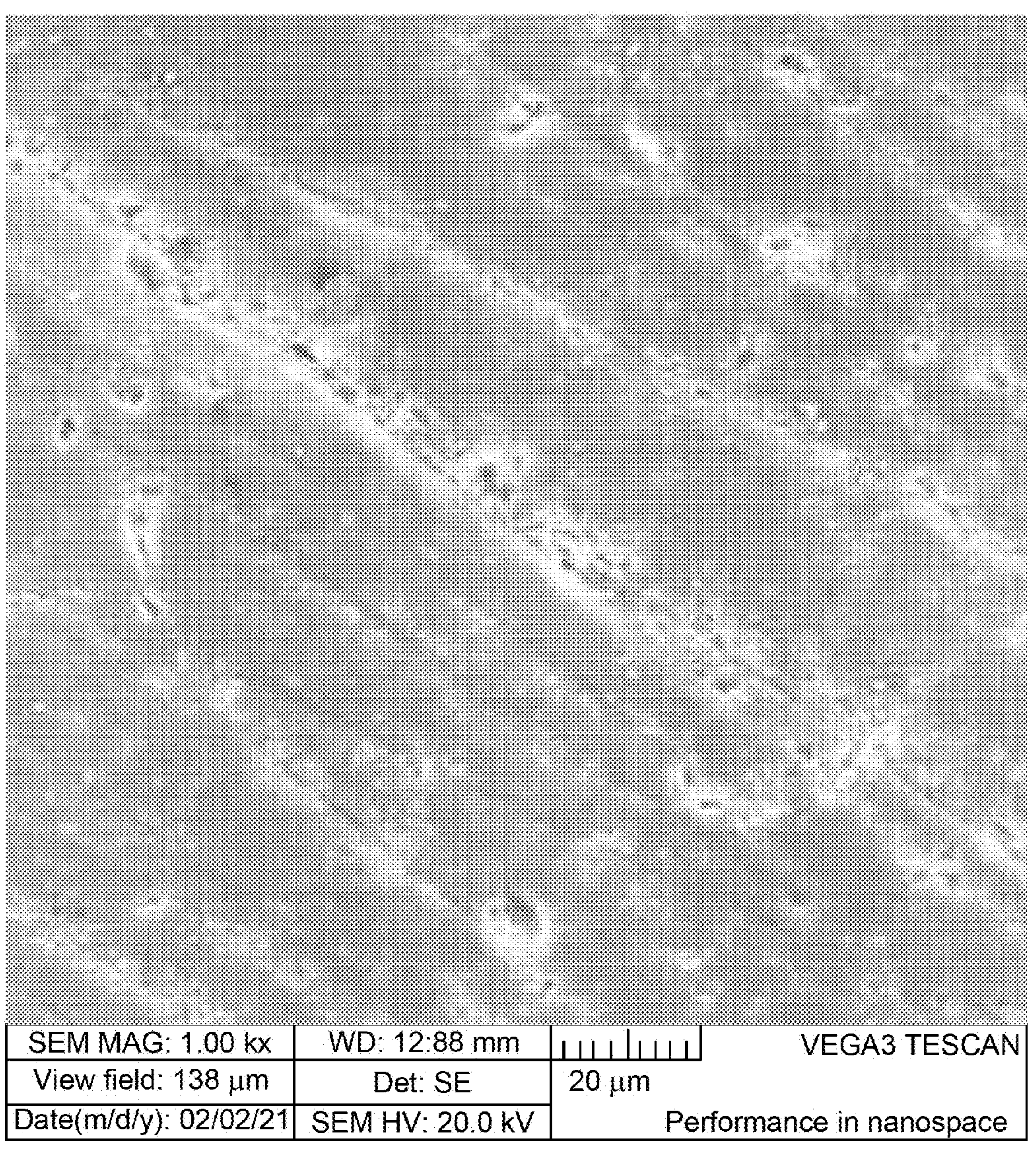
Figure 2H:
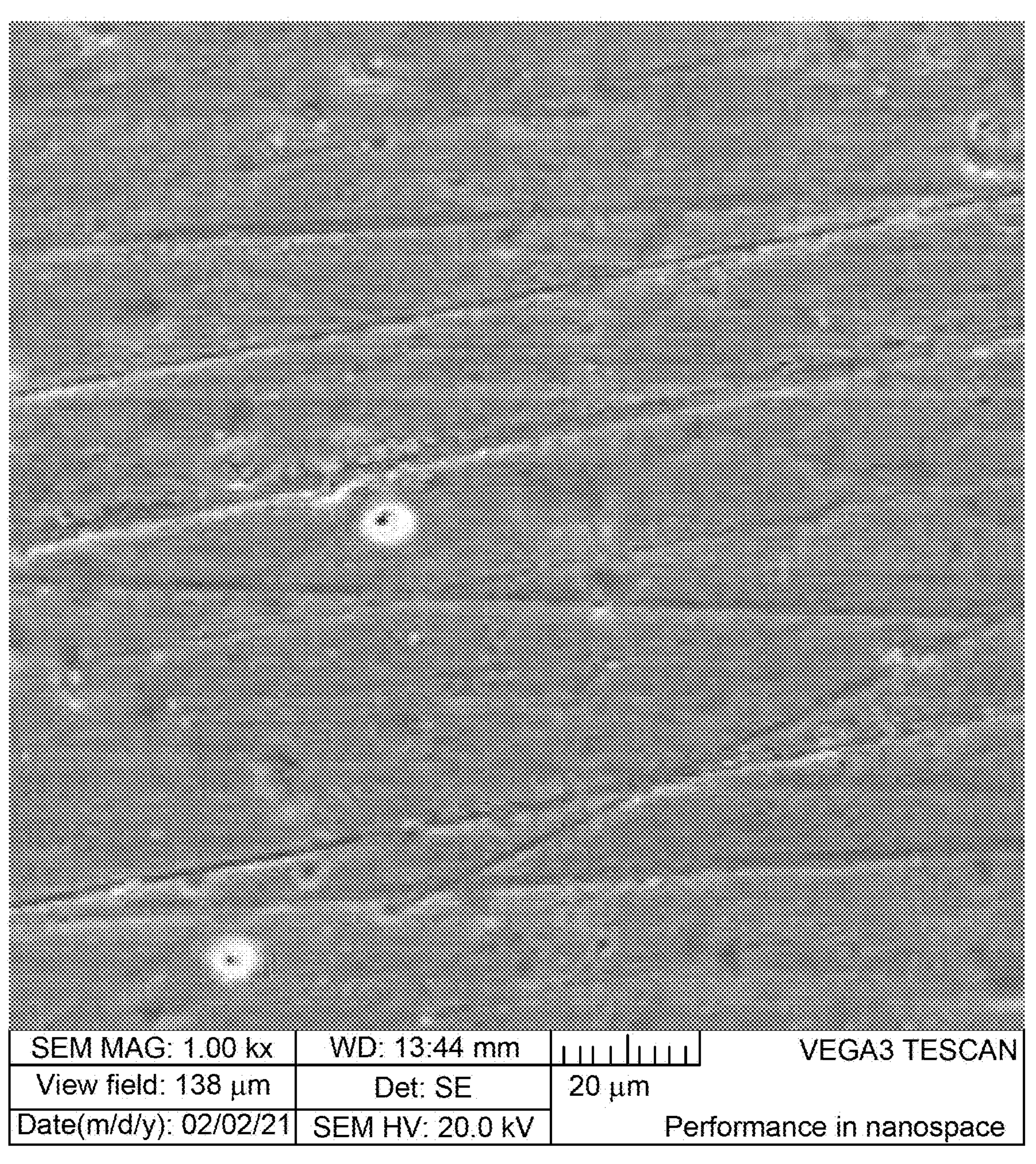
Figure 3A:
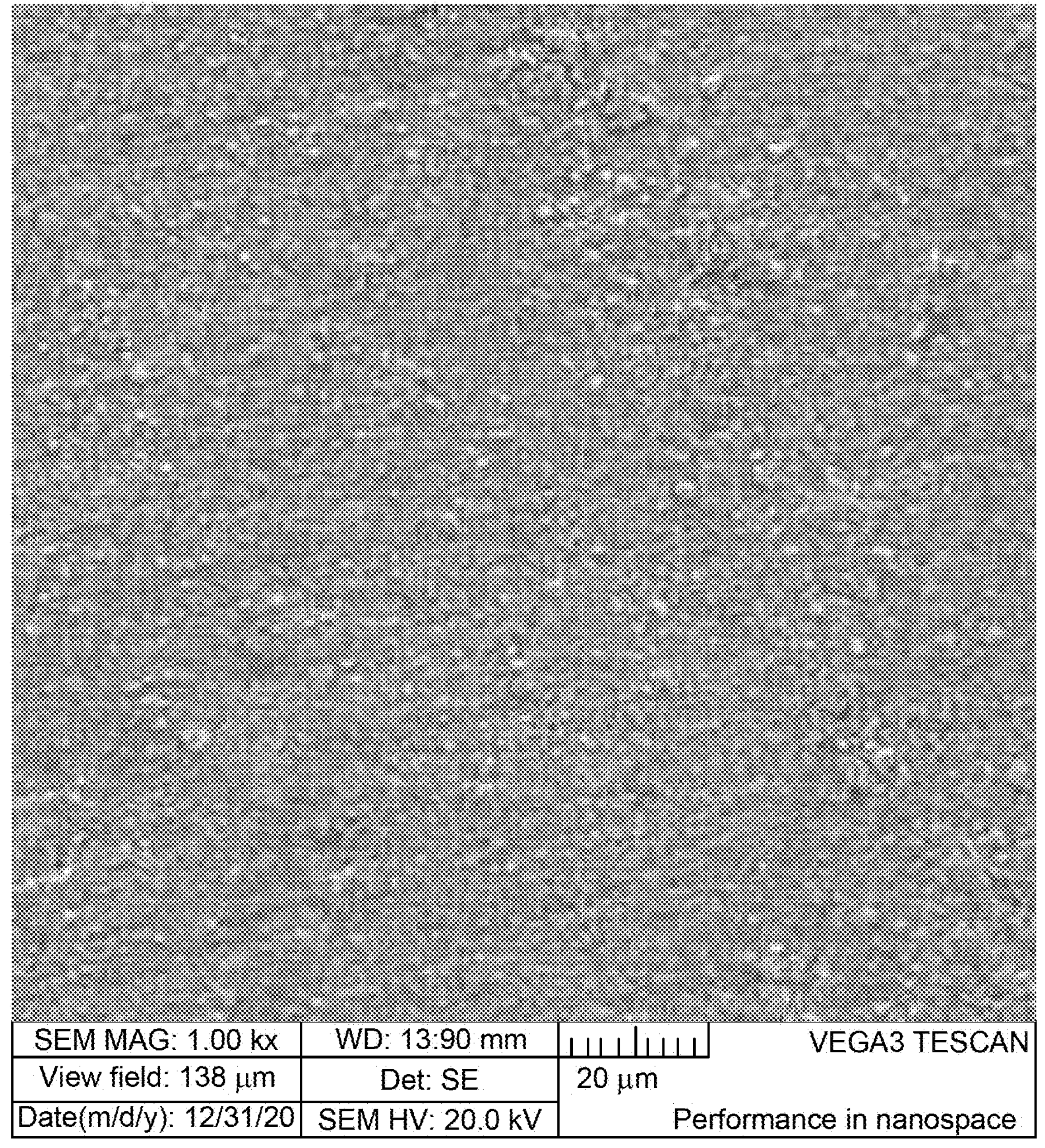
FIGS. 3A-3H are representative SEM images of surfaces of monolithic zirconia specimens, according to certain embodiments.
Figure 3B:
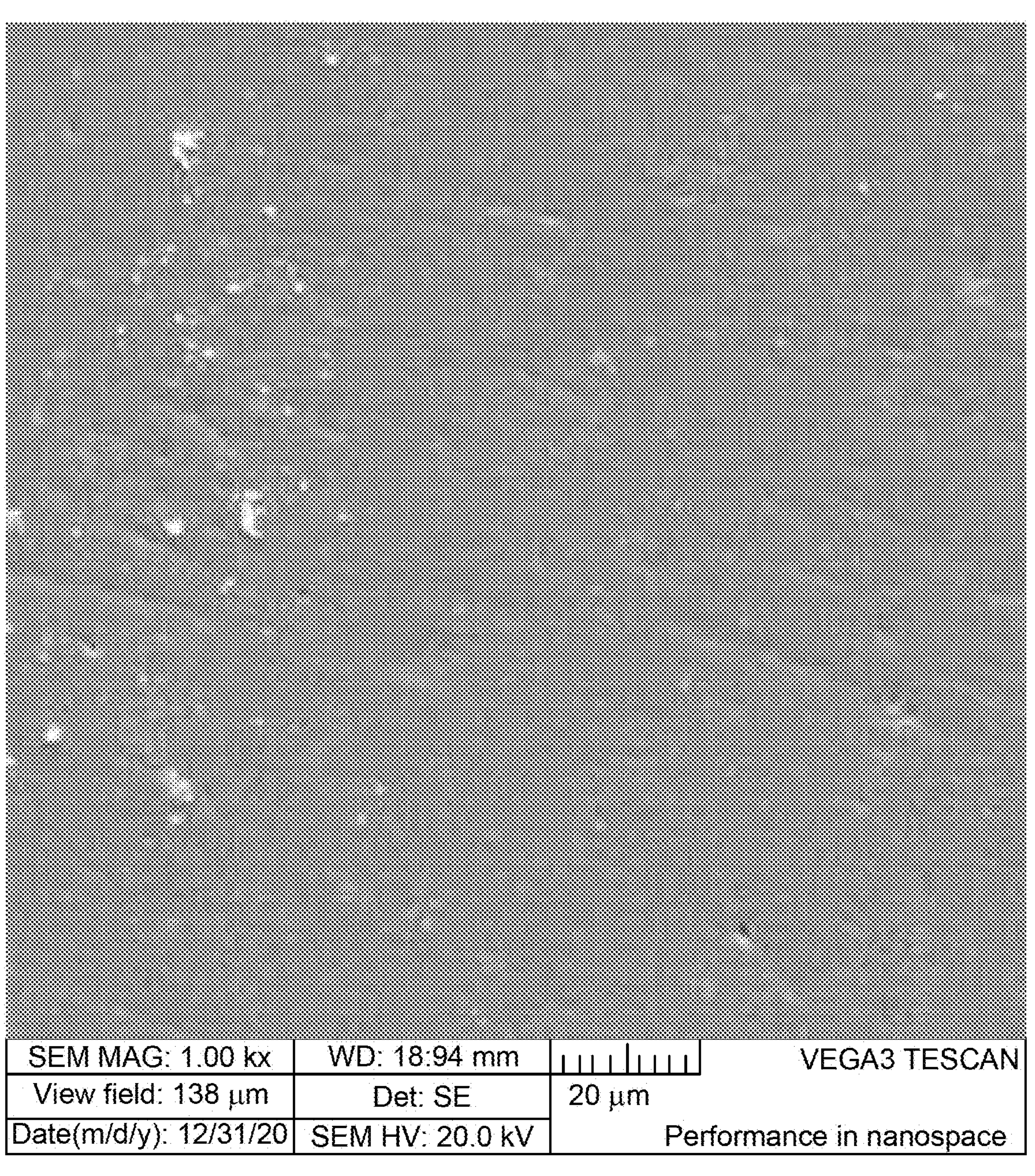
Figure 3C:
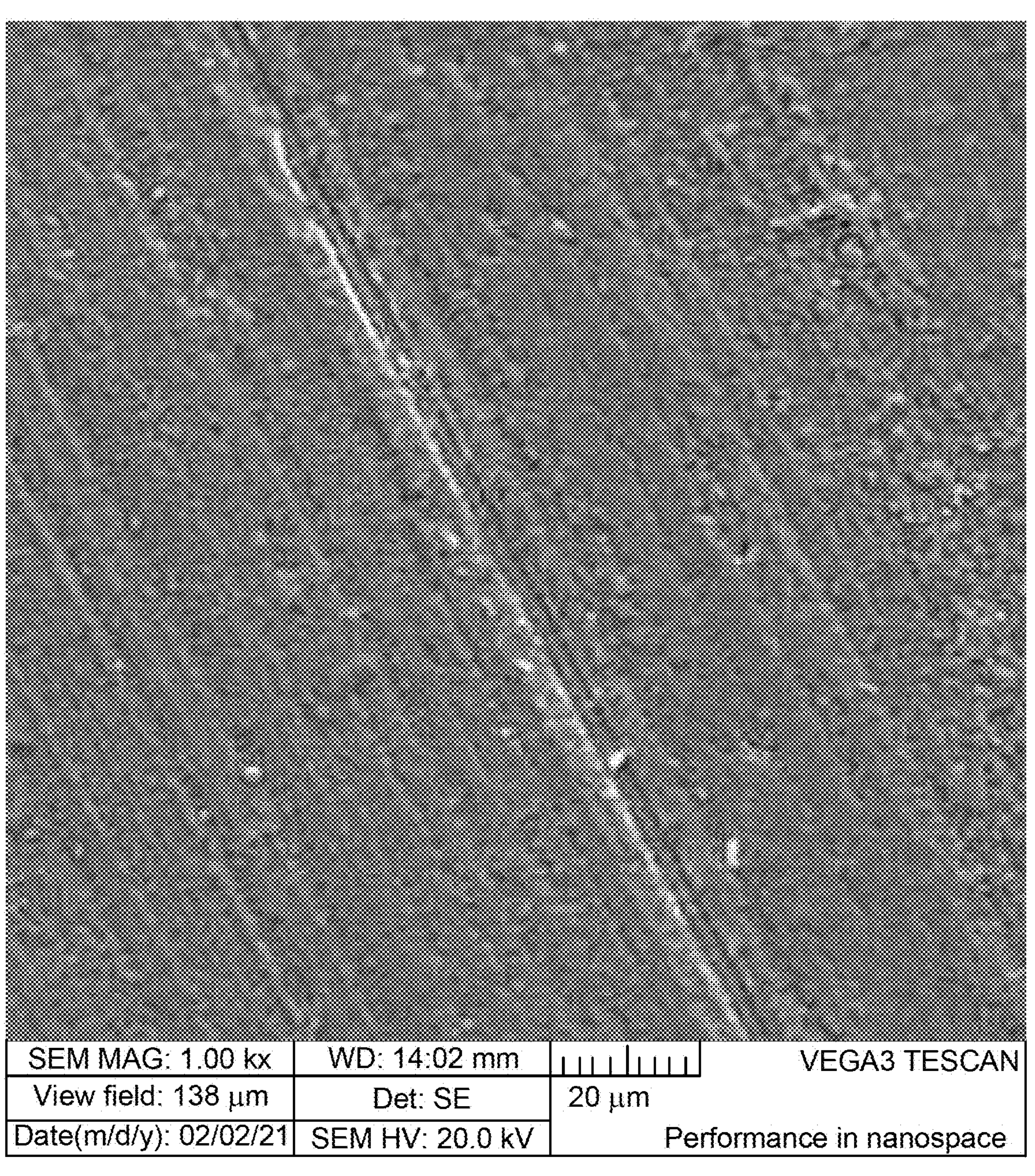
Figure 3D:
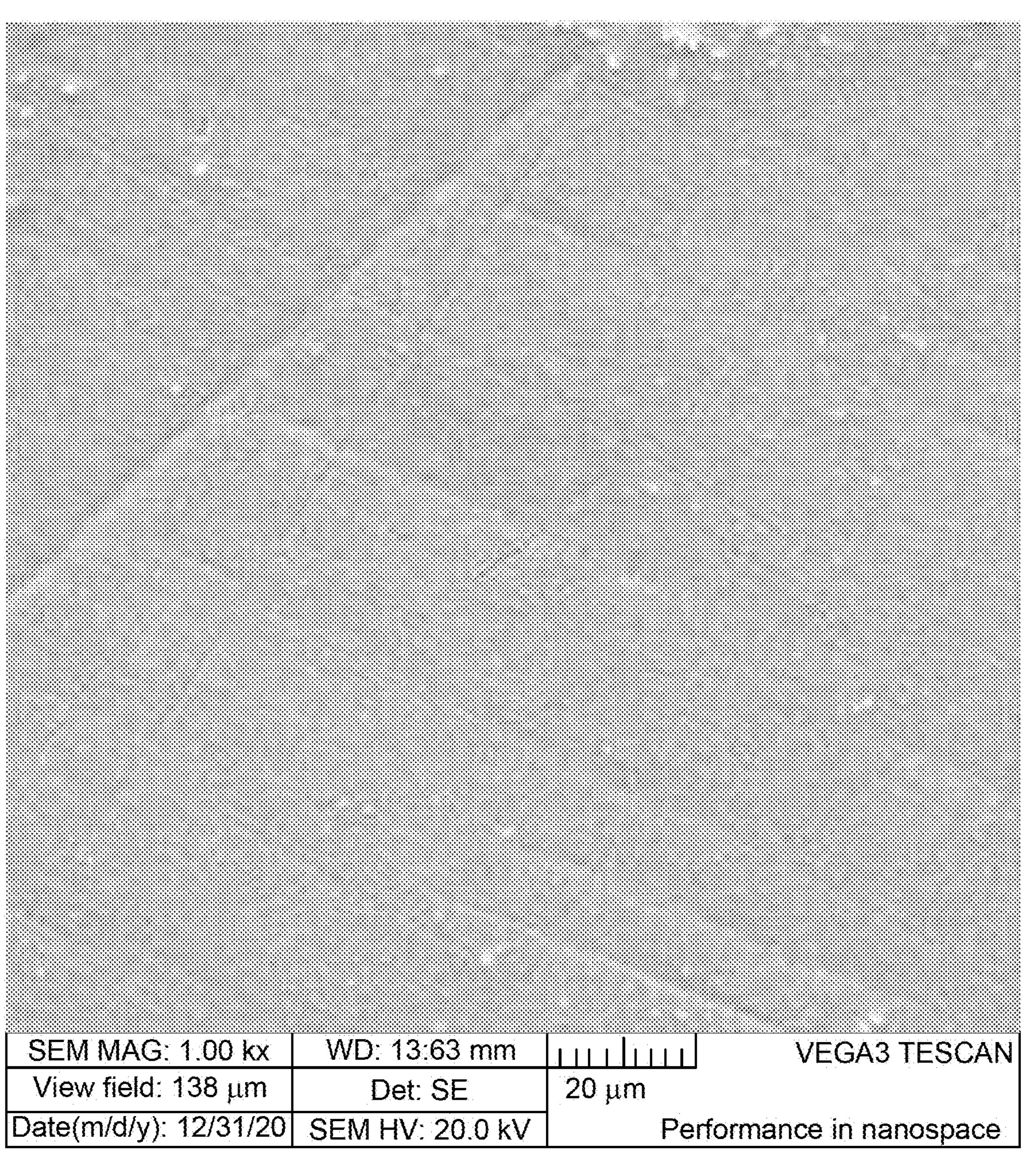
Figure 3E:
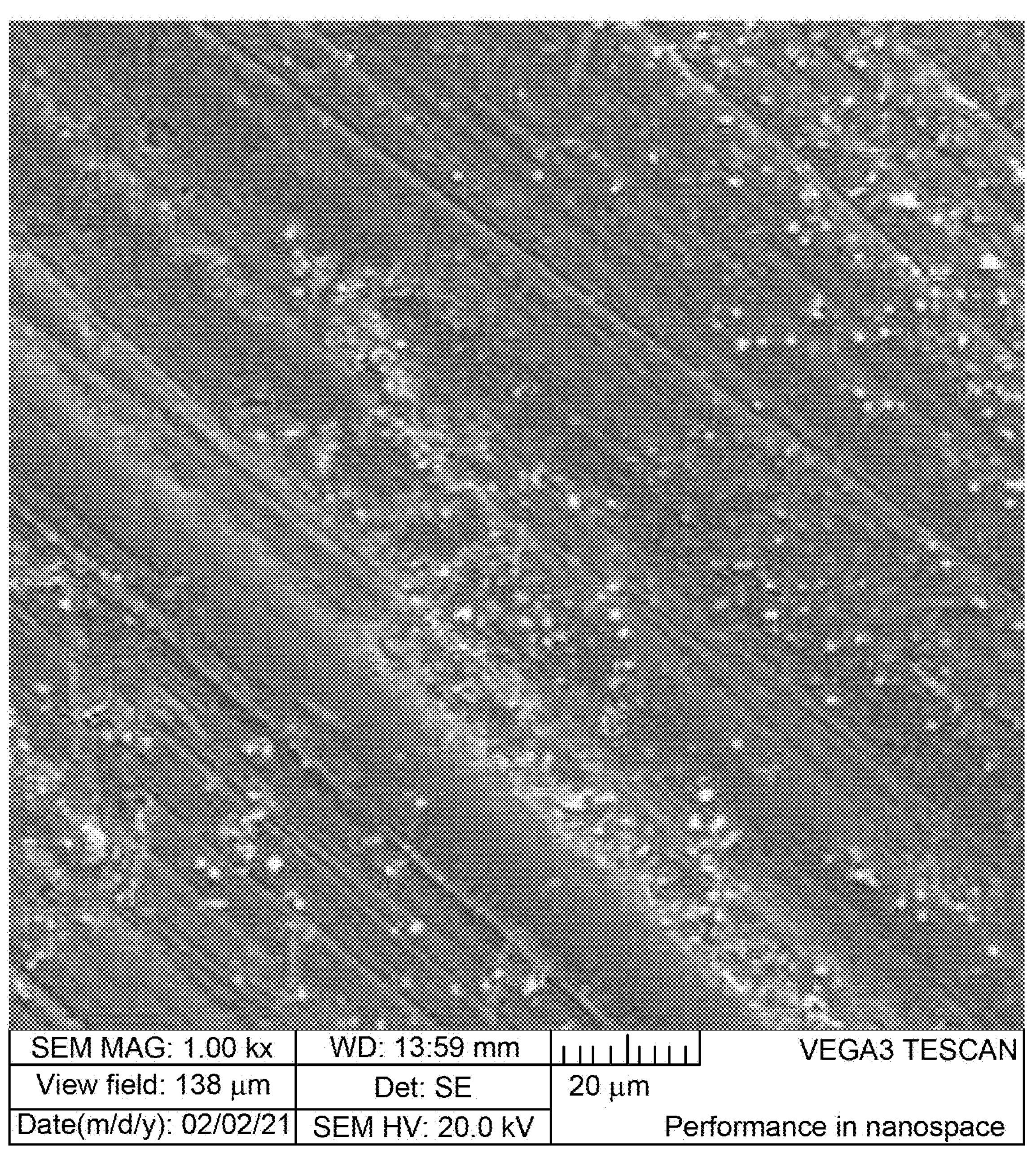
Figure 3F:
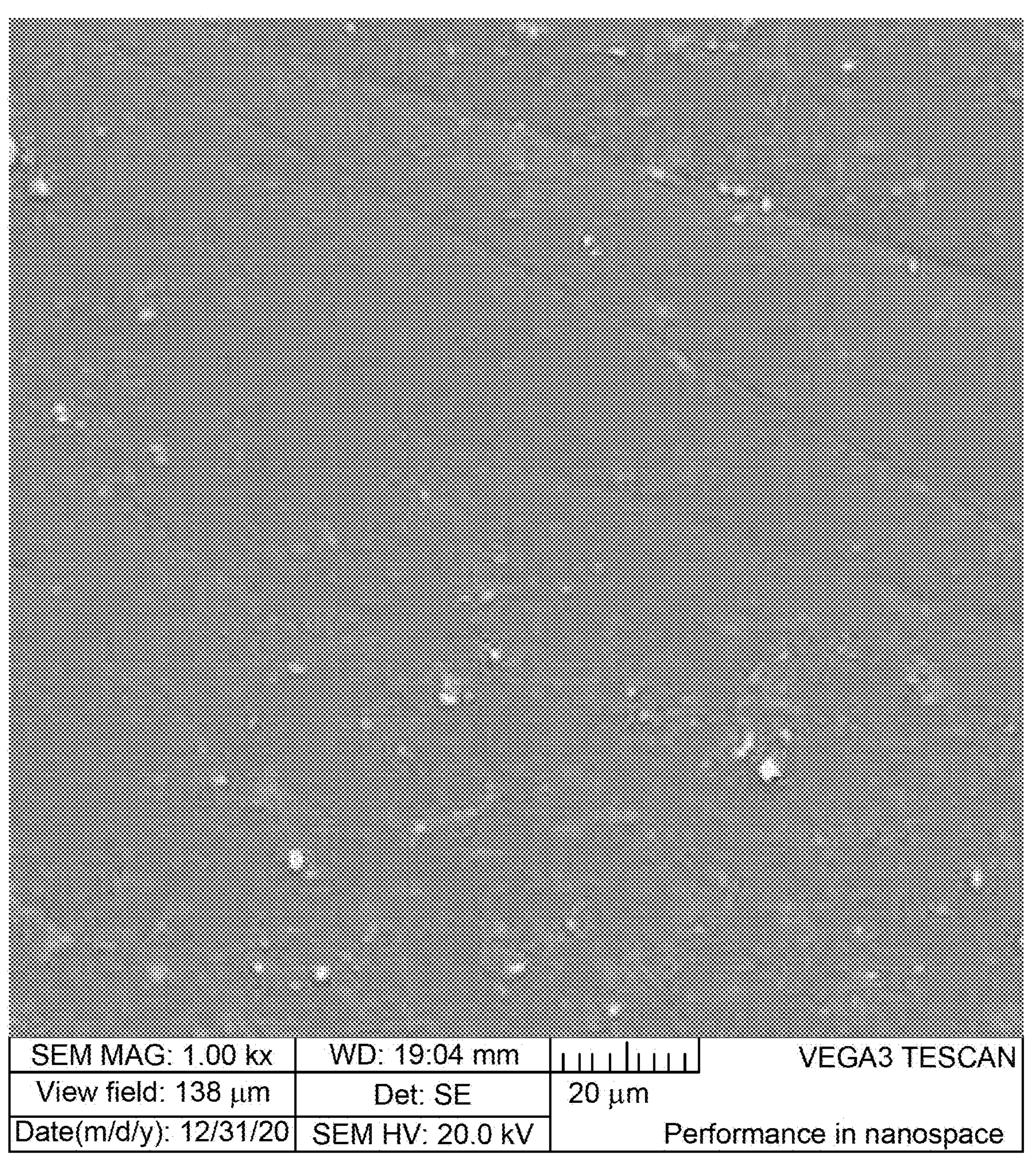
Figure 3G:
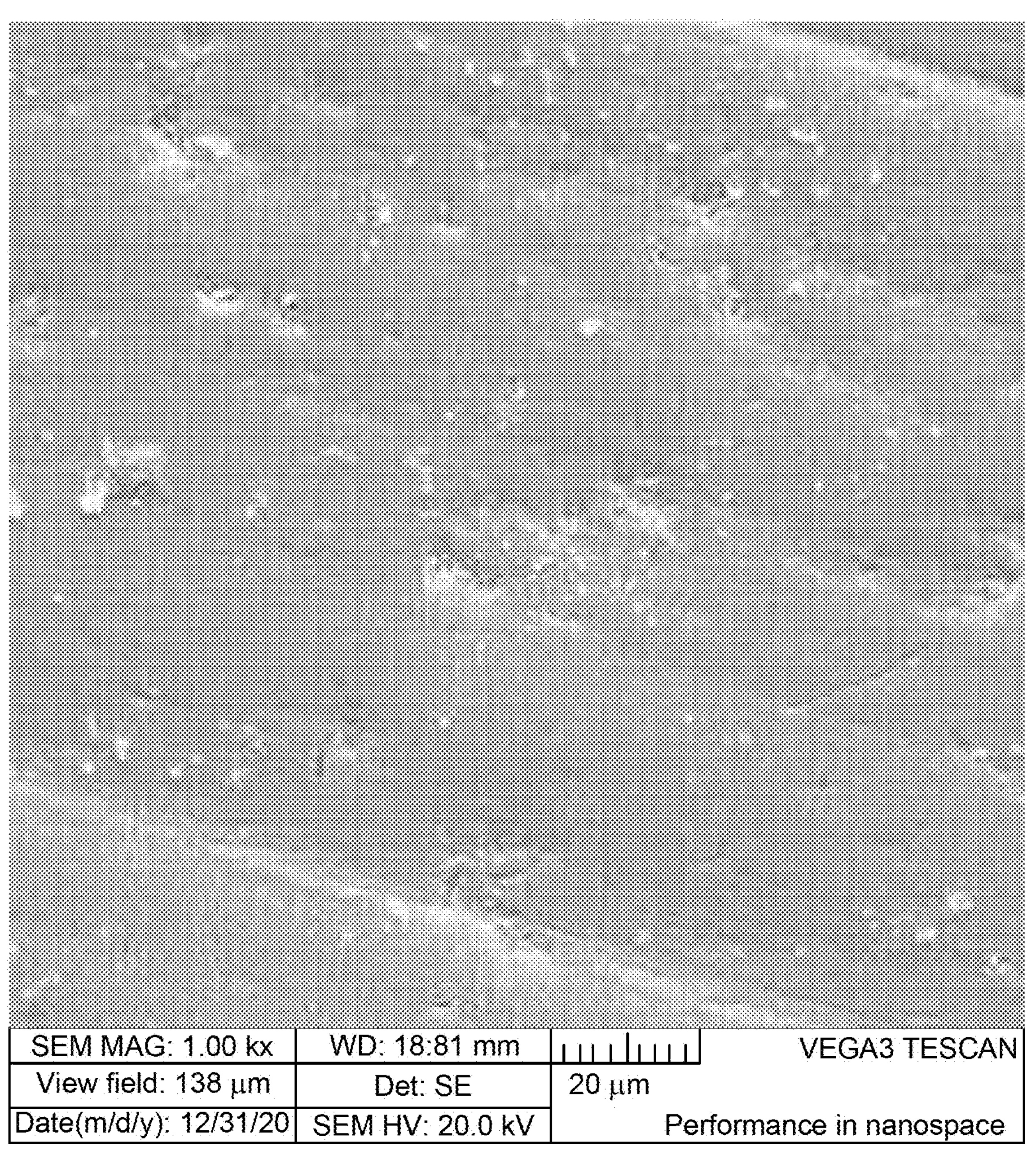
Figure 3H:
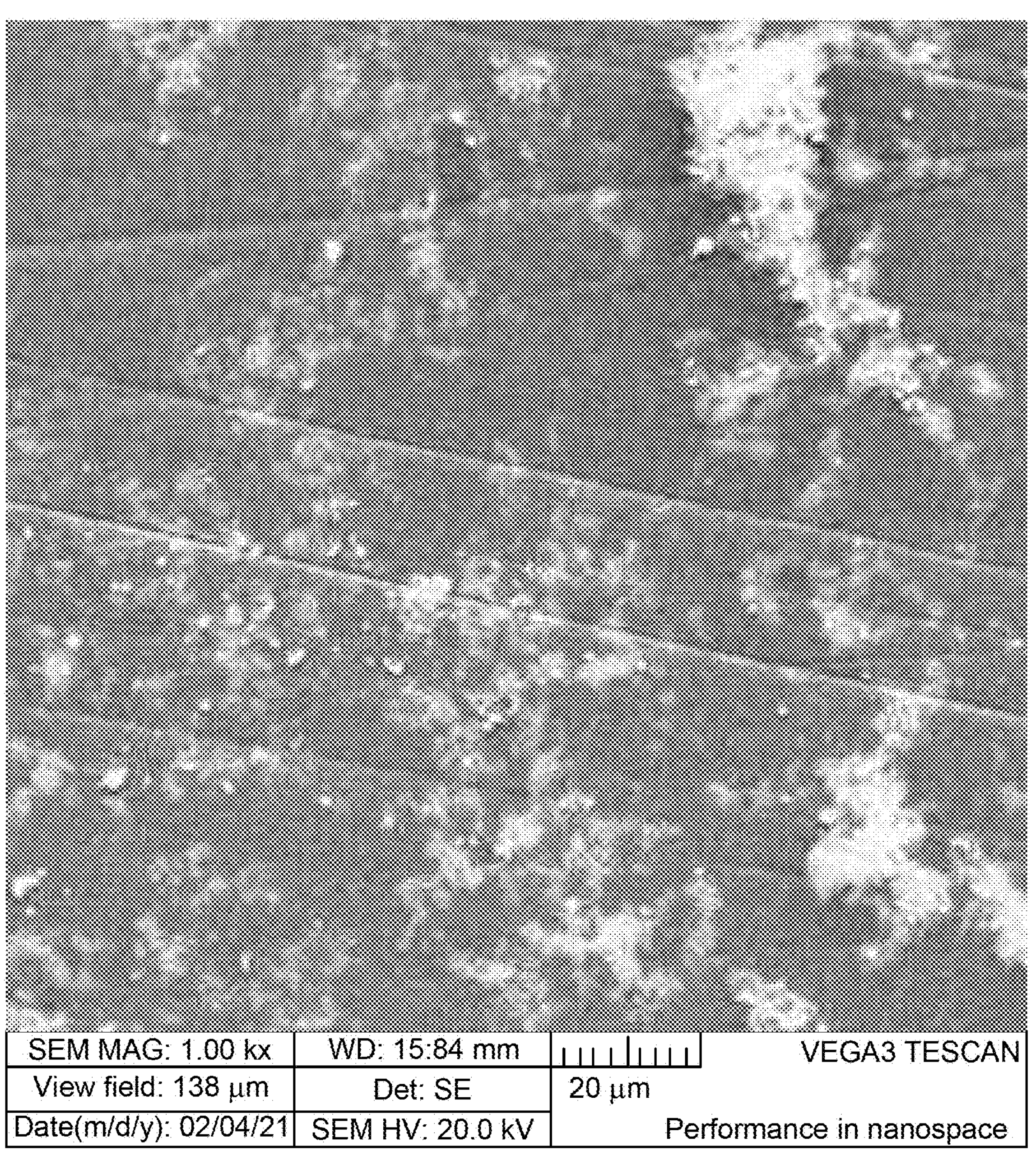

Referring to FIGS. 2A-2H and 3A-3H, SEM images of surfaces of lithium disilicate and monolithic zirconia are illustrated. The SEM confirmed the results of the surface roughness. The glazed specimens had a smooth surface texture with small voids and zero grooves or scratches (FIGS. 2B and 3B). Morphological surface changes, such as grooves and scratches were seen on the surface of ground specimens (FIGS. 2C and 3C). The surface was made progressively smoother by using the polishing techniques. Further, striations are observed under the SEM, for DPs, ZR and NZR treatments for lithium disilicate material (FIGS. 2D, 2G and 2H), and NS treatment for monolithic zirconia (FIG. 3E). The specimens of lithium disilicate and monolithic zirconia polished with ND paste (FIGS. 2F and 3F) showed less striations and fine flaws across surfaces with respect to the specimens polished with NS paste showed apparent shallow striations with remnants of nano-paste on the polished surface (FIGS. 2E and 3E). Moreover, NZR produced smooth surface with monolithic zirconia (FIG. 3H) and rough surface with lithium disilicate (FIG. 2H).

Figures 4A, 4B, 4C, 4D:
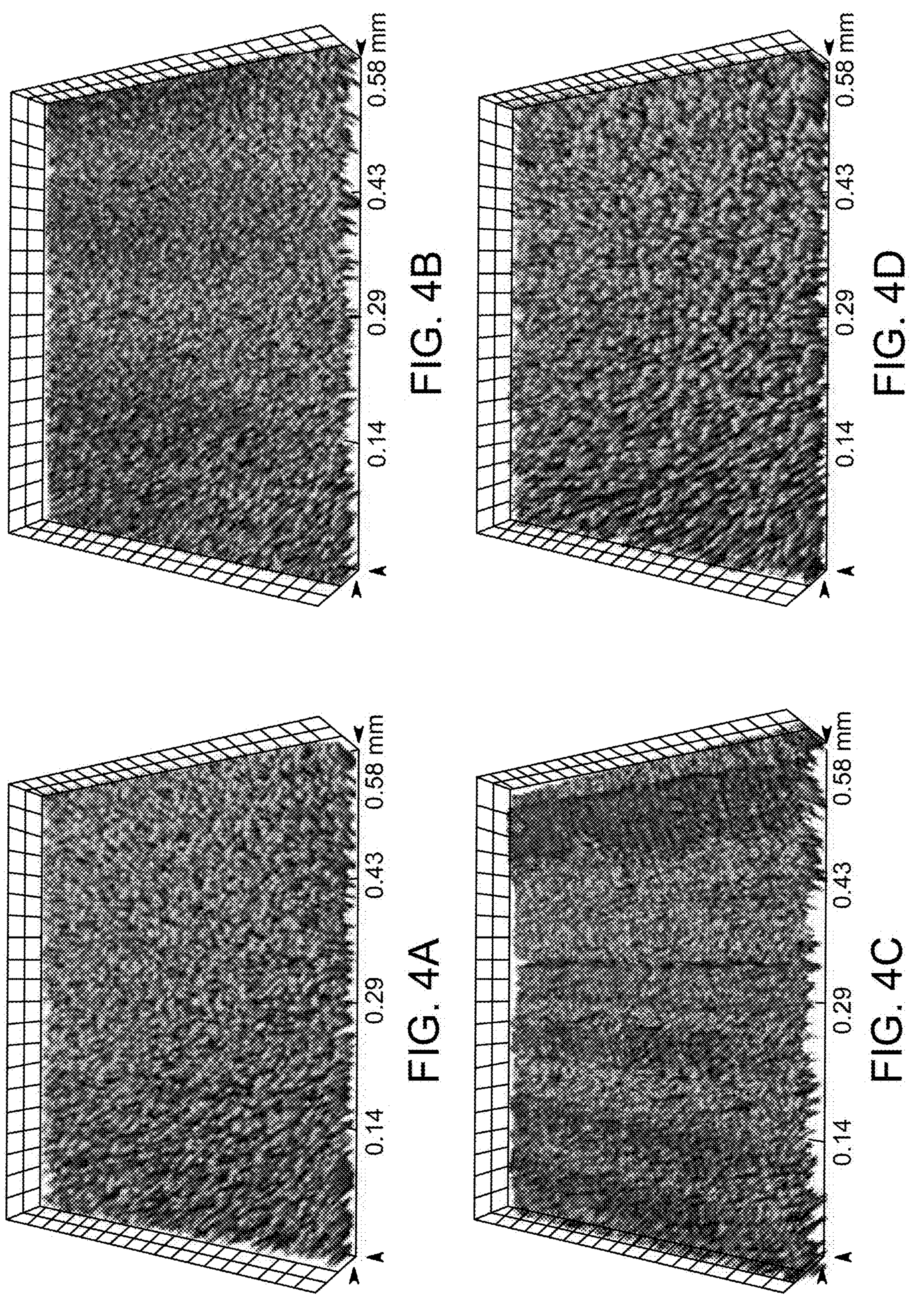
FIGS. 4A-4H are representative surface roughness images for lithium disilicate, according to certain embodiments.
Figures 4E, 4F, 4G, 4H:
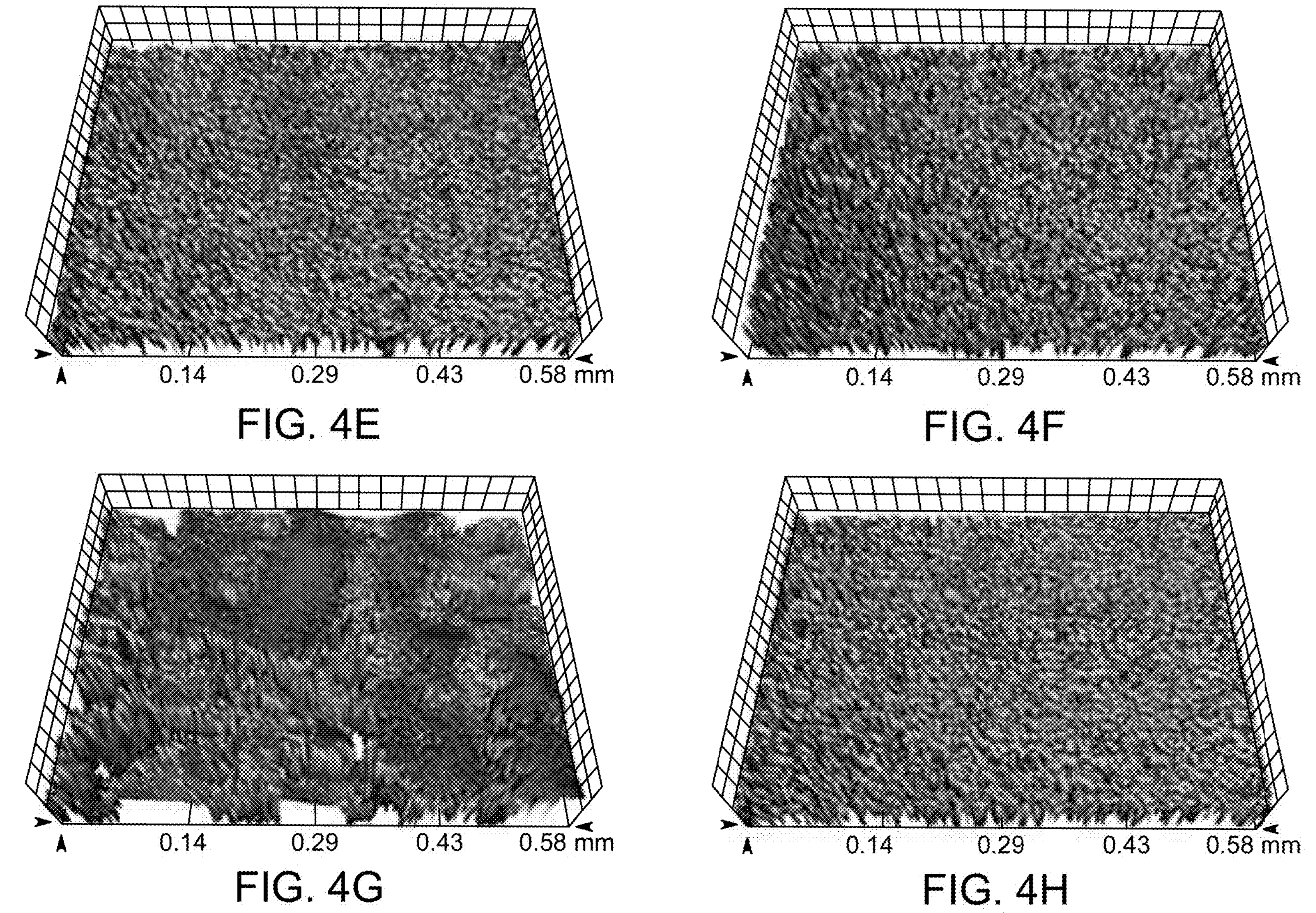
Figures 5A, 5B, 5C, 5D:
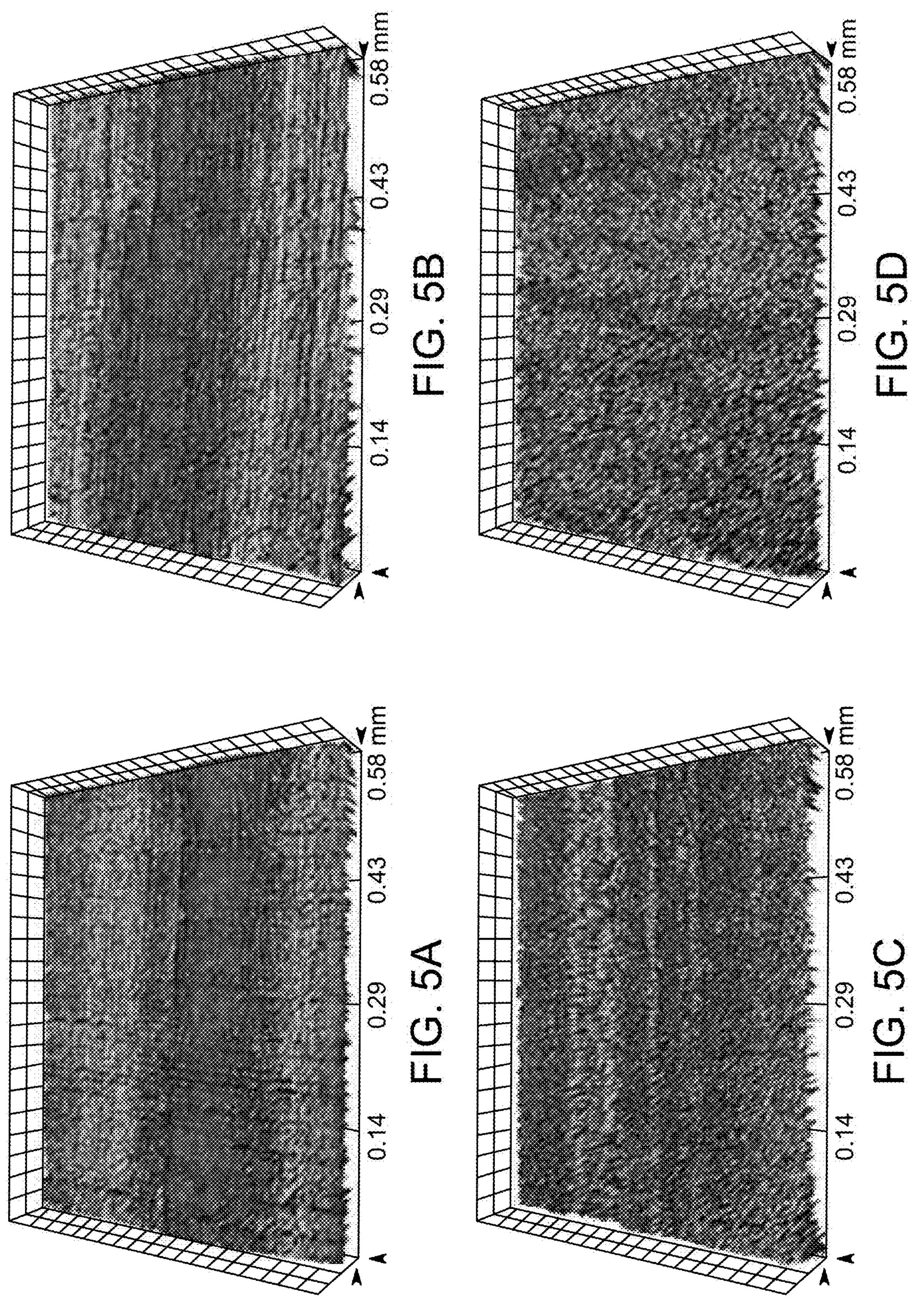
FIGS. 5A-5H are representative surface roughness images for monolithic zirconia, according to certain embodiments.
Figures 5E, 5F, 5G, 5H:
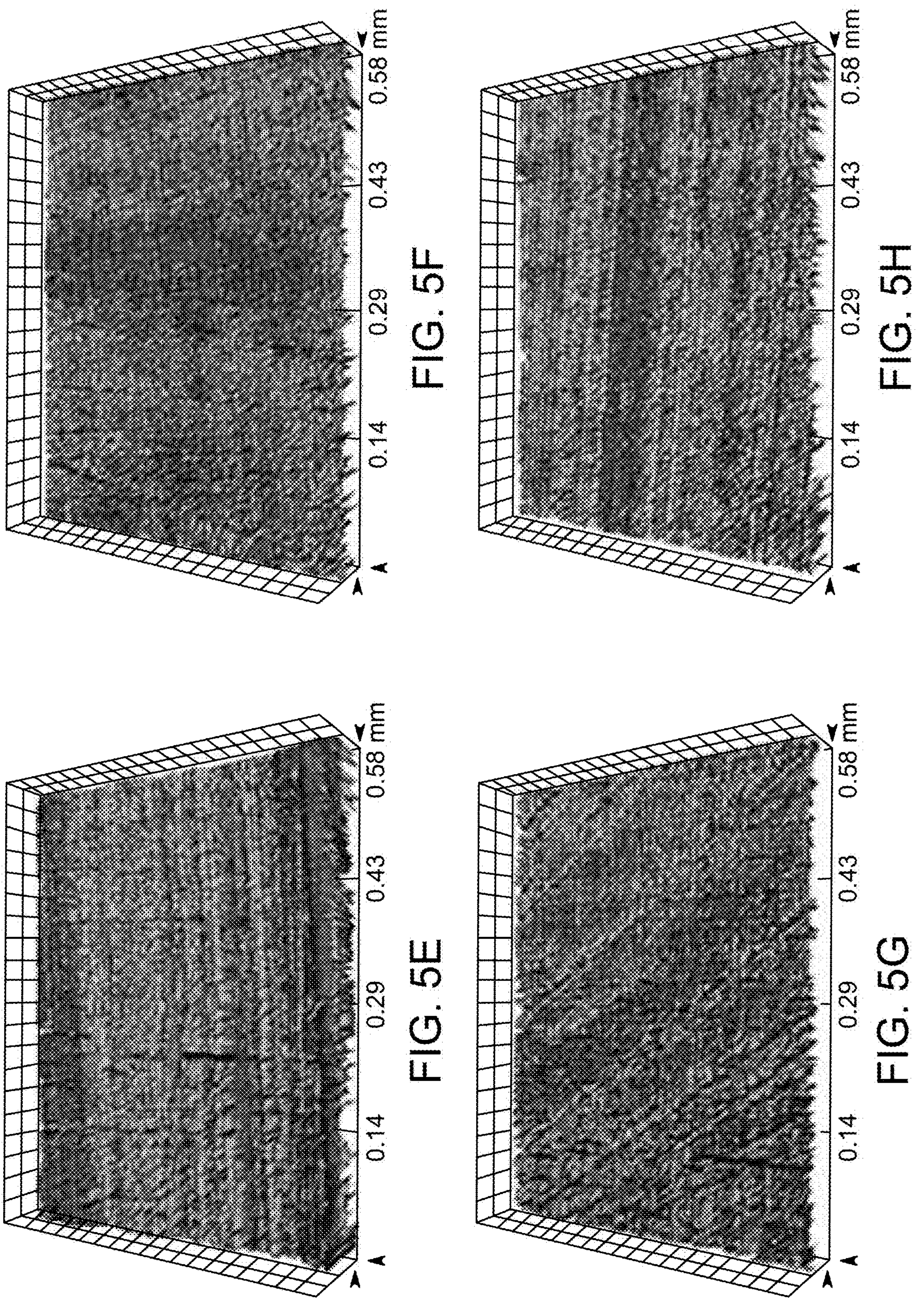

Referring to FIGS. 4A-4H and 5A-5H, representative surface roughness images for lithium disilicate and monolithic zirconia, respectively are illustrated. Positive control (FIG. 4B) and ZR (FIG. 4G) polishing techniques produced the highest irregularity in the surface as compared to all other groups of lithium disilicate. Polishing techniques produced relatively smooth surfaces of monolithic zirconia (FIGS. 5A-5H). However, unidirectional striations were seen for the positive control, the glazed, the NS, the ZR and the NZR groups (FIGS. 5B, 5C, 5E, 5G and 5H) respectively.

Example 4

The present disclosure evaluates the impact of different polishing pastes on the surface roughness of the ceramic materials. The results showed significant differences between the polishing techniques used for each ceramic material and between the ceramic materials for each polishing technique.

The polished dental ceramic surface has comparable surface roughness to a glazed surface. It was observed that glazing of lithium disilicate had no significant increase in the surface roughness compared to tested polishing techniques except positive control and ZR techniques. In addition, the positive control technique presented a significant increase in the surface roughness of monolithic zirconia in comparison to the other polishing techniques. The significant increase in the surface roughness is attributed to different polishing materials and tools used in the present techniques where polishing with the rubber prophy cup and the mixture of Colgate™ toothpaste and glycerin was used in the positive control technique, while lab-made micro-zirconia paste was applied in the ZR technique.

To have a high polished surface of the ceramic materials, the polishing material should be harder than the ceramic materials. The significant surface roughness in the positive control technique can be explained as lithium disilicate and monolithic zirconia were ground using medium grit of silicon carbide discs to simulate the clinical adjustments followed by the polishing procedure using the rubber prophy cup, the pumice slurry and the mixture of Colgate™ toothpaste and glycerin. Failure of the positive control polishing technique to reduce the surface roughness of the ceramic materials can be referred to the difference in the hardness between the polishing materials and ceramic materials.

Although similar grinding technique was applied on the ceramic materials, the lab-made polishing pastes of ND, NS and NZR groups presented mean surface roughness values close to the negative control and glazed groups. The particle size of the polishing material affects the polishing procedures. In the present disclosure, the particle size of the lab-made polishing pastes (ND, NS and NZR, FIG. 1) ranged from 12 to 19 nm. Hence, a positive influence of the lab-made polishing pastes on the surface roughness of the ceramic materials was observed. Therefore, the lab-made polishing pastes can be recommended as acceptable polishing techniques for the tested ceramic materials.

Ceramic materials can be abraded faster with large sized particles. However, the large sized particles can create rougher surface with deeper grooves. Zirconia particle size used in the ZR paste was 5 μm, which is higher than the particle size used in other pastes. Hence, ZR paste did not create smooth surfaces of feldspathic porcelain equivalent to other used polishing techniques.

The results of the present study for polishing of lithium disilicate illustrated that ND technique had the lowest surface roughness mean value with insignificant difference compared to the glazing technique and the negative control group. Diamond paste is known to create smooth surface similar to glazing or re-glazing. The thickness of plate-like diamond particles used in the present disclosure is around 30 nm or less, which is smaller than the diamond particles within commercially available diamond pastes. Furthermore, the smooth surface created by ND technique can be attributed to the unique morphology and shape of nanodiamond particles. Thus, the ND technique can be recommended to polish lithium disilicates.

SEM images showed smoother surfaces with fewer striations created by glazing techniques and the lab-made polishing pastes except ZR and NZR. The lab-made polishing pastes created insignificant surface roughness compared with the glazed and the control groups. Furthermore, the specimens treated with NS also produced fewer deep striations and traces of surface nanoclusters. Nevertheless, the specimens polished with a positive control technique had deeper scratches and rougher surfaces. Hence, the positive control technique had a significant increase in $R_a$ values.

The surface roughness value of an enamel layer in contact with opposing natural dentition is 0.64 μm. 0.64 μm value is clinically essential to determine the acceptable surface roughness level of dental restorations. The results of the present study suggest that all polishing techniques for lithium disilicate and monolithic zirconia had values below 0.64 μm except the positive control technique (0.67±0.087 μm for lithium disilicate, 0.66±0.137 μm for monolithic zirconia) and the ZR technique (0.668±0.213 μm for lithium disilicate), suggesting that the lab-made polishing pastes can be considered clinically acceptable.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of surface finishing a dental ceramic with zirconia nanoparticles, the method comprising:
- pre-polishing a surface of the dental ceramic with a pumice slurry;
- polishing the surface of the dental ceramic present in the oral cavity of the subject with a dental polishing paste comprising 60 to 90 weight percentage (wt. %) glycerin, 7.5 to 17.5 wt. % inorganic nanoparticles having a mean particle size of 5 to 25 nanometer (nm) and which are zirconia, and 2.5 to 32.5 wt. % of an additive, each based on a total weight of the dental polishing paste, to produce a polished dental ceramic, wherein during the polishing the dental polishing paste is contacted with the surface of the dental ceramic with a rotating felt cone,
- wherein the dental ceramic is formed of lithium disilicate; and
- the polished dental ceramic has a mean surface roughness of 0.350 to 0.500 micrometers (μm).

2. The method of claim 1, wherein the additive comprises at least three selected from the group consisting of a humectant, a secondary abrasive, a surfactant, a thickener, a fluoride source, a re-mineralizing agent, an anti-tartar agent, a preservative, and a flavoring agent.

3. The method of claim 1, wherein the polishing is performed at 10,000 to 25,000 revolutions per minute (rpm).

4. The method of claim 1, wherein the polishing is performed for 60 to 180 seconds(s).

5. The method of claim 1, wherein the polishing is performed using 0.5 milliliter (mL) dental polishing paste per 150 to 250 square millimeter ($mm^2$) of the surface of the dental ceramic.

6. The method of claim 5, wherein the dental polishing paste is used in 2 to 6 aliquots applied at regular time intervals throughout a duration of the polishing.

7. The method of claim 1, wherein the pre-polishing is performed at 10,000 to 25,000 rpm and for 30 to 90 seconds.

8. The method of claim 1, wherein the pre-polishing is performed using 0.2 mL pumice slurry per 150 to 250 $mm^2$ of the surface of the dental ceramic.

9. The method of claim 1, wherein the pre-polishing is performed using a rubber prophy cup.

* * * * *